(12) United States Patent
Koblasz

(10) Patent No.: US 7,714,728 B2
(45) Date of Patent: May 11, 2010

(54) USING RFID TO PREVENT OR DETECT FALLS, WANDERING, BED EGRESS AND MEDICATION ERRORS

(75) Inventor: Arthur Koblasz, Atlanta, GA (US)

(73) Assignee: GT Angel, LLC, Atlanta, GA (US)

( * ) Notice: Subject to any disclaimer, the term of this patent is extended or adjusted under 35 U.S.C. 154(b) by 479 days.

(21) Appl. No.: 11/651,117

(22) Filed: Jan. 8, 2007

(65) Prior Publication Data

US 2007/0159332 A1  Jul. 12, 2007

Related U.S. Application Data

(60) Provisional application No. 60/756,679, filed on Jan. 7, 2006.

(51) Int. Cl.
G08B 23/00 (2006.01)
G08B 21/00 (2006.01)

(52) U.S. Cl. .............. 340/573.1; 340/573.7; 340/572.7; 340/286.07

(58) Field of Classification Search ........................ None
See application file for complete search history.

(56) References Cited

U.S. PATENT DOCUMENTS

| | | |
|---|---|---|
| 4,067,005 A | 1/1978 | Levy et al. |
| 4,228,426 A | 10/1980 | Roberts |
| 4,539,559 A | 9/1985 | Kelly et al. |
| 4,539,560 A | 9/1985 | Fleck et al. |
| 4,583,084 A | 4/1986 | Henderson et al. |
| 4,814,751 A | 3/1989 | Hawkins et al. |
| 4,858,622 A | 8/1989 | Osterweil |
| 4,907,845 A | 3/1990 | Wood |
| 4,947,152 A | 8/1990 | Hodges |

(Continued)

FOREIGN PATENT DOCUMENTS

EP    1063624    12/2000

(Continued)

OTHER PUBLICATIONS

European Examination Report for European Application 07716384.8 mailed Apr. 20, 2009, 5 pages.

(Continued)

*Primary Examiner*—Daniel Wu
*Assistant Examiner*—Nay Tun
(74) *Attorney, Agent, or Firm*—Hope Baldauff Hartman, LLC

(57) ABSTRACT

Systems, methods, and devices for using body-worn RFID tags related instrumentation located in the premises where a monitored person is located to prevent or detect specific types of movements of the person, such as falls from which the person has not recovered, wandering, bed egress, attempted room egress, and medication errors. The body-worn RFID tags may include an upper body RFID tag located in a wrist band and a lower body RFID tag located in a sock worn by the monitored person. The RFID instrumentation located in the premises may include one or more antennas located in the floor, door, bed frame, and mattress. The systems may also activate response actions upon detecting specified movements, such as sending an alert message to a patient monitoring system, activating an alarm, activating an camera, and/or playing a recorded message to the person.

21 Claims, 15 Drawing Sheets

U.S. PATENT DOCUMENTS

| | | |
|---|---|---|
| 5,146,206 A | 9/1992 | Callaway |
| 5,523,742 A | 6/1996 | Simkins et al. |
| 5,600,305 A | 2/1997 | Stafford et al. |
| 5,751,214 A | 5/1998 | Cowley et al. |
| 5,838,223 A | 11/1998 | Gallant et al. |
| 5,838,240 A | 11/1998 | Johnson |
| 5,844,488 A | 12/1998 | Musick |
| 5,877,675 A | 3/1999 | Rebstock et al. |
| 6,078,561 A | 6/2000 | Kakinuma |
| 6,100,804 A | 8/2000 | Brady et al. |
| 6,590,498 B2 | 7/2003 | Helms |
| 6,600,418 B2 * | 7/2003 | Francis et al. ............ 340/572.1 |
| 6,703,930 B2 | 3/2004 | Skinner |
| 6,703,935 B1 | 3/2004 | Chung et al. |
| 6,707,381 B1 | 3/2004 | Maloney |
| 6,747,561 B1 | 6/2004 | Reeves |
| 6,753,782 B2 | 6/2004 | Power |
| 6,753,783 B2 * | 6/2004 | Friedman et al. ......... 340/573.7 |
| 6,774,800 B2 | 8/2004 | Friedman et al. |
| 6,812,824 B1 | 11/2004 | Goldinger et al. |
| 6,837,432 B2 | 1/2005 | Tsikos et al. |
| 6,847,892 B2 | 1/2005 | Zhou et al. |
| 6,853,303 B2 | 2/2005 | Chen et al. |
| 6,861,993 B2 | 3/2005 | Waldner |
| 6,883,710 B2 | 4/2005 | Chung |
| 6,888,459 B2 | 5/2005 | Stilp |
| 6,894,614 B2 | 5/2005 | Eckstein et al. |
| 6,899,476 B1 | 5/2005 | Barrus et al. |
| 6,903,656 B1 | 6/2005 | Lee |
| 6,935,560 B2 | 8/2005 | Andreasson et al. |
| 6,985,870 B2 | 1/2006 | Martucci et al. |
| 2002/0067270 A1 | 6/2002 | Yarin et al. |
| 2002/0183979 A1 * | 12/2002 | Wildman .................... 702/188 |
| 2002/0196146 A1 * | 12/2002 | Moore ...................... 340/572.7 |
| 2003/0052788 A1 * | 3/2003 | Kwong-Tai Chung .... 340/573.1 |
| 2003/0160698 A1 | 8/2003 | Andreasson et al. |
| 2004/0010390 A1 | 1/2004 | Kelly, Jr. et al. |
| 2005/0035862 A1 | 2/2005 | Wildman et al. |
| 2005/0121505 A1 | 6/2005 | Metz et al. |
| 2006/0001545 A1 * | 1/2006 | Wolf ....................... 340/573.1 |

FOREIGN PATENT DOCUMENTS

| | | |
|---|---|---|
| EP | 1166686 | 1/2002 |
| EP | 1269502 | 1/2003 |
| GB | 2133660 A | 7/1984 |
| GB | 0327138 | 5/2005 |
| JP | 7131392 | 5/1995 |
| WO | WO9620681 A1 | 11/1996 |
| WO | WO9812997 A1 | 2/1998 |
| WO | WO9936021 A1 | 7/1999 |
| WO | WO02078513 A2 | 10/2002 |
| WO | WO02091297 A1 | 11/2002 |

OTHER PUBLICATIONS

International Search Report for PCT Application PCT/US2007/000319 mailed Sep. 11, 2007, 18 pages.

* cited by examiner

USING RFID TO PREVENT OR DETECT FALLS, WANDERING, BED EGRESS AND MEDICATION ERRORS

REFERENCE TO RELATED APPLICATION

This application claims priority to U.S. Provisional Patent Application Ser. No. 60/756,679, filed Jan. 7, 2006, which is incorporated herein by reference.

TECHNICAL FIELD

The present disclosure relates generally to RFID technology and, more particularly, to the use of RFID to prevent or detect falls, wandering, bed egress, attempted or actual room egress, and medication access by a monitored person.

BACKGROUND

Falls are a serious health problem for all types of people, especially elderly people in all countries. M. Tinetti interviewed 336 people who were 75 yrs or older, living at home in New Haven, Conn. (Reference: *Predictors and prognosis of inability to get up after falls among elderly persons*. JAMA, January 1993, v. 269(1), p. 65-70). These elderly adults claimed that during the previous twelve months, 32% had one or more falls, and 24% had serious injuries including 6% with fractures. In a comparable study, A. Blake contacted 1042 people 65 yrs or older, living at home in England (Reference: *Falls by elderly people at home: prevalence and associated factors*. Age and Aging, 1988, v. 17, p. 365-372). During the preceding twelve months, 35% had one or more falls, i.e. 53% due to tipping, 8% due to dizziness, 6% due to blackouts and 19% uncertain. According to R. Cumming some medications increase the risk of multiple falls/yr, e.g. Diazepam (3.7× more likely), Diltiazem (1.8× more likely), Diuretics (1.8× more likely) and Laxatives (2.1× more likely) (Reference: *Medications and multiple falls in elderly people: The St. Louis OASIS Study*. Aging, November 1991, v. 20(6) p. 455-461).

According to J. Sutton, falls among elderly hospital patients in England are the most common type of self-inflicted accident (Reference: *Patient Accidents in hospitals: incidence, documentation and significance*. British Journal of Clinical Practice, March-April, 1994, v. 48(2), p. 63-66). J. Yaretzky studied a population of 609 hospital patients (447 females+162 men) in Israel with a mean age of 84 yrs (Reference: *Falls in elderly patients in an institution*. School of Medicine, Tel Aviv University, December 1999, v. 121(12), p. 503-505). During a 2-month period, 18% of the patients had one or more serious falls. Older patients fell mostly while getting in and out of bed. Yaretzky also concluded that sleeping pills and psychotropic drugs increase the likelihood of falls. During the next decade of continuing hospital cutbacks and increasing patient-to-nurse ratios, the front-line nurses will require more assistive devices to increase their efficiency and ability to detect patient falls.

To prevent falls, there is a separate need to detect when a patient confined to bed is about to get out of bed or has gotten out of bed, i.e. bed egress. There is also a separate need to detect when a patient is wandering into areas in which the patient is not authorized to access.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE EMBODIMENTS

Figure 1:
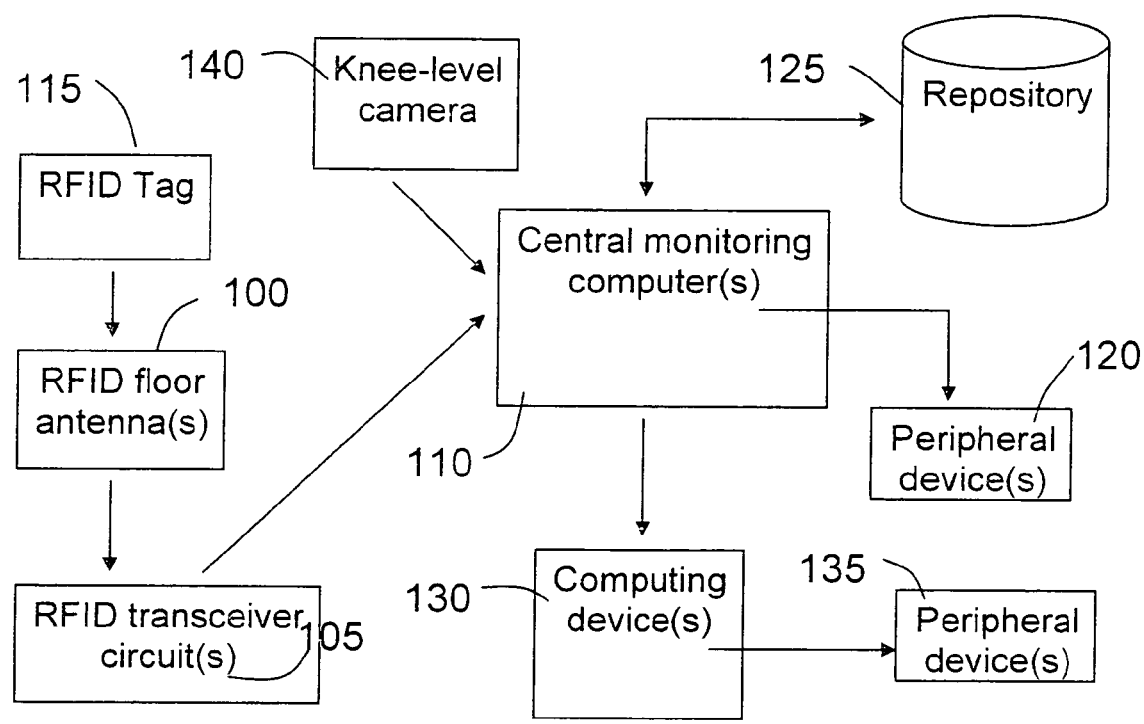
FIG. 1 illustrates an exemplary embodiment of a system that may be used to detect and alert of possible falls or bed egress using RFID technology.

The present invention may be embodied in a wide range of systems, methods, and devices for using body-worn RFID tags related instrumentation located in the premises where a monitored person is located to prevent or detect specific types of movements of the person, such as falls from which the person has not recovered, wandering, bed egress, attempted room egress, and medication errors. The body-worn RFID tags may include an upper body RFID tag located in a wrist band and a lower body RFID tag located in an ankle band or sock worn by the monitored person. The RFID instrumentation located in the premises may include one or more antennas located in the floor, door, bed frame, and mattress. The systems may also activate response actions upon detecting specified movements, such as sending an alert message to a caregiver, activating an alarm, activating a camera, and playing a recorded message to the person.

For example, the system detects room egress by detecting that one or more RFID tags worn by the monitored person has moved past a door antenna associated with a door, door frame or door knob providing egress to the premises. In this case, the response action may include transmission of a room egress message to the patient monitoring system and activation of a camera configured to record movements of the monitored person following the room egress. Once the basic principles of the invention are understood through the explanation of specific examples such as this room egress application described above, many other types of movement detection and response actions may be devised to meet the needs of specific patients and applications. In particular, patient wondering and other types of erratic conduct such as attempted window, failure of the monitored person to return to an assigned room at bedtime, extended periods out of bed or in the bathroom at night, and the like can be detected and responded to with automated announcements, alert messages, intercom communications and so forth. The system may also be used to detect and monitor other types of activities, such as medication delivery; meal delivery, tray pickup, staff response times to alert messages and patient calls, unauthorized room entry by staff personnel, unusual movements indicative of physical violence or abduction, and so forth.

Detection of Falls

An RFID tag may be associated with a body part of a patient that is usually not in proximity to the floor and that may be in proximity to the floor if a fall has occurred (an "RFID fall tag"). A patient may be any person and not limited to a patient in a hospital, alternative care facility, or nursing home environment. The body part may be, for example, any one or more of a patient's wrist, arm, waist, hip, neck, head, or ear. The RFID fall tag may be attached to, or contained inside, a wrist bracelet, a portion of an upper body garment such as a pocket, a necklace, a waistband such as a belt, jewelry such as an earring or a necklace, a wristband, a wristwatch, an armband, an elbow pad, a hairclip, a finger ring, a headband, a knee pad, a hearing-aid, a hip pocket, a high sock, a stocking, or garment attachments such as a lapel pin, a garment clip, a button, or a safety pin. RFID fall tags may be attached to an upper body garment by being enclosed by sewn-in, buttoned in, or Velcro pockets, or they may be attached to the upper body garment by buttons, snap-on buttons, or an adhesive such as Velcro. RFID fall tags may be used on both wrists to increase the accuracy of the fall detection and to also allow the same tags to be used to detect when a patient is wandering, as described below. Although more invasive, an RFID fall tag may also be imbedded below the skin, such as a sub-dermal implant or a trans-dermal device, or attached to the skin using a biocompatible tape or adhesive. The RFID tag can also be attached to a standard hospital ID tag which may also display the patient's printed name, barcode label, and or other information. An exemplary RFID fall tag may be either a "passive" or "active" RFID tag.

One or more RFID antennas may be located in proximity to the floor ("RFID floor antennas 100"). Exemplary embodiments of various RFID floor antennas 100 are described below with respect to FIGS. 8 through 13. The RFID antenna may be underneath, inside, or near any component of a floor, such as the floor covering, floor backing material, underlayment, padding, or subfloor, which may be made of plywood or concrete. The floor covering may comprise rubber, linoleum, vinyl, fiber reinforced vinyl, plastic, metal, wood, a composite material, simulated wood such as laminated panels, rug, or carpet. The floor covering may also include tile, including tiles made of, for example, ceramic material, porcelain material, granite, or marble. The floor covering may also include a mat, which may be made of rubber, linoleum, plastic, carpet, or vinyl, and may include a laundry mat, a rug, a welcome mat, or a bathmat. Padding may comprise one or more of polyurethane, polyethylene, polystyrene, polystyrene foam, rubber, latex, or any other type of cushioning material. Floor backing material may comprise any durable nonconductive material, for example, jute, fiberglass, or non-woven (or woven) bonded polyethylene, polyester, or polypropylene fibers.

Exemplary RFID floor antennas 100, although they can be placed anywhere, may be placed where falls are likely to occur, such as alongside a bed, a doorway, a bathtub, a toilet, or near steps. Because falls can occur in a shower or bathroom, one or more RFID floor antennas 100 may be located within the flooring or side of a tub, or in the flooring beneath a tub, whether it is a shower tub or a bathtub. The tub may be fiberglass, cast iron, steel, or ceramic but non-conductive materials are preferred if the antenna(s) are located below the tub. Additionally, an RFID floor antenna 100 may be imbedded inside or attached to the underside of a floor mat next to the tub and/or toilet to detect falls in these areas. Alternatively, or additionally, the mat may be a waterproof mat, which allows it to be located on the inside surface of a tub.

One or more of the RFID floor antennas 100 may be coupled to one or more RFID Transceiver circuits 105. Preferably, the RFID transceiver circuits 105 may be positioned as close as possible to each RFID floor antenna 100. In one embodiment, to reduce the number of RFID transceiver circuits 105 needed, multiple RFID floor antennas 100 may be coupled to one RFID transceiver circuit 105 via a switch or multiplexer, which may be electronic or mechanical. The switch or multiplexer may be continuously switched between each RFID floor antenna 100.

Each RFID transceiver circuit 105 may have computing capabilities, as well as communications capabilities for communicating, either directly or through a network, with one or more computing devices, which may include a computer, for example one or more central monitoring computers 110. In one exemplary embodiment, the central monitoring computer 110 may be any type of computing device and may include either hardware, software, or a combination of both, that may make the central monitoring computer 110 operative to perform the functions described herein, or originate instructions that are used to perform the functions described herein. These instructions may reside on local memory, RAM, compact disc, thumb drive, or any other type of computer readable medium. The central monitoring computer 110 may be located anywhere in the facility, including at an attendant station, a monitoring station, a central monitoring station, on the person of an attendant, at a medicine cabinet, or bedside, such as inside furniture, for example a bedside nightstand. In one exemplary embodiment, one central monitoring computer 110 is used for the entire facility. In another exemplary embodiment, each floor may have a central monitoring computer 110. In yet another exemplary embodiment, the central monitoring computer 110 may be part of a home security system.

In one exemplary embodiment employing hardwire, RFID transceiver circuits 105 may be coupled to the central monitoring computer 110 via flat wires under the flooring and/or multi-lead cables in the walls and or ceilings.

In another embodiment employing wireline communications, an RFID transceiver circuit 105 may be coupled to the central monitoring computer 110 via the AC power lines that provide power to the RFID transceiver circuit 105. The RFID transceiver circuit 105 may transmit high-frequency modulations superimposed onto the AC power lines that provide power to the RFID transceiver circuit. In such an embodiment, the central monitoring computer 110 receives communications from RFID transceiver circuits 105 by continuously monitoring the power lines and decoding the high-frequency encoded voltage signals. In one exemplary configuration, the central monitoring computer 110 has access to all the electrical circuits in all of the patient rooms, and this computer 110 communicates directly with all of the RFID transceiver circuits 105.

The RFID transceiver circuit 105 may additionally include wireless communications components that allow the RFID transceiver circuit 105 to communicate with the central monitoring computer 110 wirelessly, for example using cellular, WIFI (e.g., 802.11a), Ultra Wideband, or any other wireless scheme. In another wireless embodiment, the RFID transceiver circuit may communicate via an ultrasound transmitter that generates an inaudible ultrasound signal (for example, the carrier frequency could indicate the room number and amplitude or pulse modulations of the carrier frequency could indicate the specific location of the patient, and any variations of either may indicate a fall condition). A monitoring computer may be set up to monitor this ultrasonic signal. The monitoring computer may include a microphone and additional electronics that continuously listen for audible or ultrasound alarms in the same or nearby rooms.

In another exemplary embodiment, the RFID floor antenna 100 and RFID transceiver circuit 105 may be powered exclusively by battery. The battery may be re-chargeable. When the battery is low, the transceiver circuit may send out an alarm code.

The central monitoring computer(s) 110 may be coupled with one or more peripheral devices 120, which may comprise audible and visual display devices. These devices may comprise speakers, printers, monitors, TVs, or flat-panel displays. The central monitoring computer 110 may be coupled with one or more other computing devices 130 that may comprise a desktop computer, or portable computing devices such as a laptop computer, a handheld computer, a pager, a cellular phone, or a PDA. A computing device 130 may also be coupled with a peripheral device 135, or even other computing devices (not shown), for example, through a network. The computing devices may also have wireless communications capabilities. Peripheral and computing devices 130 may be located at an attendant station, a monitoring station, a central monitoring station, on the person of an attendant, at a medicine cabinet, or bedside, such as inside furniture, for example a bedside nightstand.

The central monitoring computer 110 may also be coupled with one or more repositories 125 that contain patient records. Such a repository 125 may be, for example, a database residing on some type of computer readable medium, such as a hard drive, flash memory, optical disk, or magnetic tape. In doing so, the central monitoring computer 110 may communicate directly with the repository 125 if the repository 125 is local, or with a networked server (not pictured) associated with that repository 125.

An exemplary method for detecting falls involves, in response to an RFID tag being in proximity to an RFID antenna associated with a floor, determining whether the RFID tag remains in proximity to the RFID antenna for a predetermined period, and if the predetermined period has elapsed, performing an action resulting in the generation of an alert indicating that a patient may have fallen. Such an exemplary method, the details of which are described below, may be performed, for example, by one or more computers, including but not limited to a central monitoring computer 110, or one or more computers or peripheral devices that receive a communication from the central monitoring computer 110.

If an RFID tag 115 (which may be an RFID fall tag as described above) worn by a patient, regardless of whether it is active or passive, comes into proximity with an RFID floor antenna 100, the RFID floor antenna 100 may receive a signal from that RFID tag 115. The proximity can be a range that is preset. One of ordinary skill will appreciate that the range may be any range practical to determine whether a person wearing an RFID fall tag has fallen. An example of such a detection range is zero to two feet.

In an exemplary embodiment, the RFID transceiver circuit 105 coupled to the RFID floor antenna 100 processes the signal received by the RFID floor antenna 100 and communicates with a central monitoring computer 110.

The signal originating from the RFID tag 115 may contain identification information such as a binary number or some other unique identifier. This identification information may be transmitted to the central monitoring computer 110 by the RFID transceiver circuit 105. The central monitoring computer 110 may also use the identification information to obtain patient information stored in a local, or networked, repository 125. It may do this, for example, by querying the repository 125.

The central monitoring computer 110 may also be operative to determine whether the RFID tag 115 has remained in proximity to the RFID floor antenna 100 for a predetermined period. For example, the central monitoring computer 110 may wait until multiple signals originate from the RFID tag 115 before taking action. If a signal is received from an RFID tag 115 several times, for example several times within a three minute timeframe, then this condition may be an indication that a patient has fallen, as opposed to merely tying his or her shoes. Once a predetermined period has elapsed in which one or more signals originating from an RFID tag 115 have been received, the central monitoring computer 110 may perform an action resulting in the generation of an alert indicating that a patient may have fallen, as described below.

Although a particular care center, hospital, or facility may use exclusively RFID tags that are associated with a body part of a patient that is usually not in proximity to the floor, and which may be in proximity to the floor if a fall has occurred (i.e., an "RFID fall tag"), it is contemplated that RFID tags associated with a part of the body that normally is in proximity to the floor may also be used in the same environment. For example, as mentioned below, RFID tags may be associated with the foot to detect wandering. Thus, if RFID tags other than RFID fall tags are used, another step in the fall detection process may be to determine whether the RFID tag 115 from which the signal originates is an RFID fall tag. This determination may occur before, after, or contemporaneously with the determination as to whether the RFID tag 115 has remained in proximity to the RFID floor antenna 100 for a predetermined period.

The identification information contained in the signal received from the RFID tag 115 and communicated by the RFID transceiver circuit 105 can be used to determine whether the signal that originated from the RFID tag 115 is from an RFID fall tag. An RFID fall tag may be assigned an indicator, such as the first digit of a binary code, that designates it as a fall tag. Alternatively, a non-RFID fall tag may be assigned an indicator, such as the first digit of the binary code, that designates that it is either not an RFID fall tag, or perhaps an indicator that designates that it is some other type of tag. In yet another embodiment, RFID fall tags and other RFID tags may transmit signals at different frequencies. For example, an RFID fall tag may emit a signal at 134.2 kilohertz, while other RFID tags may emit signals at 13.56 megahertz. Regardless, if the central monitoring computer 110 receives a signal from an RFID transceiver 105 coupled to an antenna 100 in communication with a tag 115, it can use the fall indicator associated with the RFID tag 115 to determine whether a fall may have occurred. The central monitoring computer 110 may also use a look-up table containing the identification information associated with the RFID tag 115 to determine whether that RFID tag 115 is or is not an RFID fall tag. In this situation, if the RFID tag 115 is determined to be a fall tag, and once a predetermined period in which one or more signals originating from the RFID tag 115 have been received has elapsed, the central monitoring computer 110 may perform an action resulting in the generation of an alert indicating that a patient may have fallen.

An action resulting in the alert may be controlling or communicating with one or more peripheral devices 120, and/or computing devices 130, which may also be coupled with other peripheral devices 135. The alert may be visual, audible, or vibratory, such as a vibration from a pager. A computing device 130, after receiving a communication from the central monitoring computer 110, may also communicate with any peripheral devices 135 associated with it to generate such an alert. A computing device 130, after receiving a communication from the central monitoring computer, may also send a communication to one or more other computing devices (not shown) that can generate such an alert via peripheral devices coupled with those computing devices. This configuration of computer and peripheral devices allows the resulting product to be customized or changed easily by each institution using the equipment to detect falls. For example, some RFID fall tags 115 may trigger an alert after 60 seconds of being detected near the floor and other RFID fall tags 115 can be designated to trigger an alert after 30 seconds. In a preferred embodiment of the invention, the alert details are displayed at a nurses' station and if an attendant response is not detected at the nurses' station, the alert details are then automatically forwarded to an assigned attendant's wireless communication device.

An exemplary action resulting in the generation of an alert that the central monitoring computer 110 may perform may be to control or communicate with one or more peripheral devices 120 that may be a visual display, which may be any type of visual display, including those mentioned above. As one of ordinary skill in the art would understand, a computer can communicate with a visual display, and the communications can contain commands, instructions, or information that result in the visual display generating a visual alert indicating that a patient may have fallen. Other information generated and displayed may include, but is not limited to, the name of the patient, an alphanumeric identification assigned to the patient, the room number of the patient, and the location of the RFID tag that triggered the alert (and thus the location of the patient if the RFID tag is on the patient's person), and any other relevant patient record information. Such information may be obtained by the central monitoring computer 110, which may match the identification information associated with the RFID tag 115 with information obtained from the patient's records in repository 125.

Figure 2:
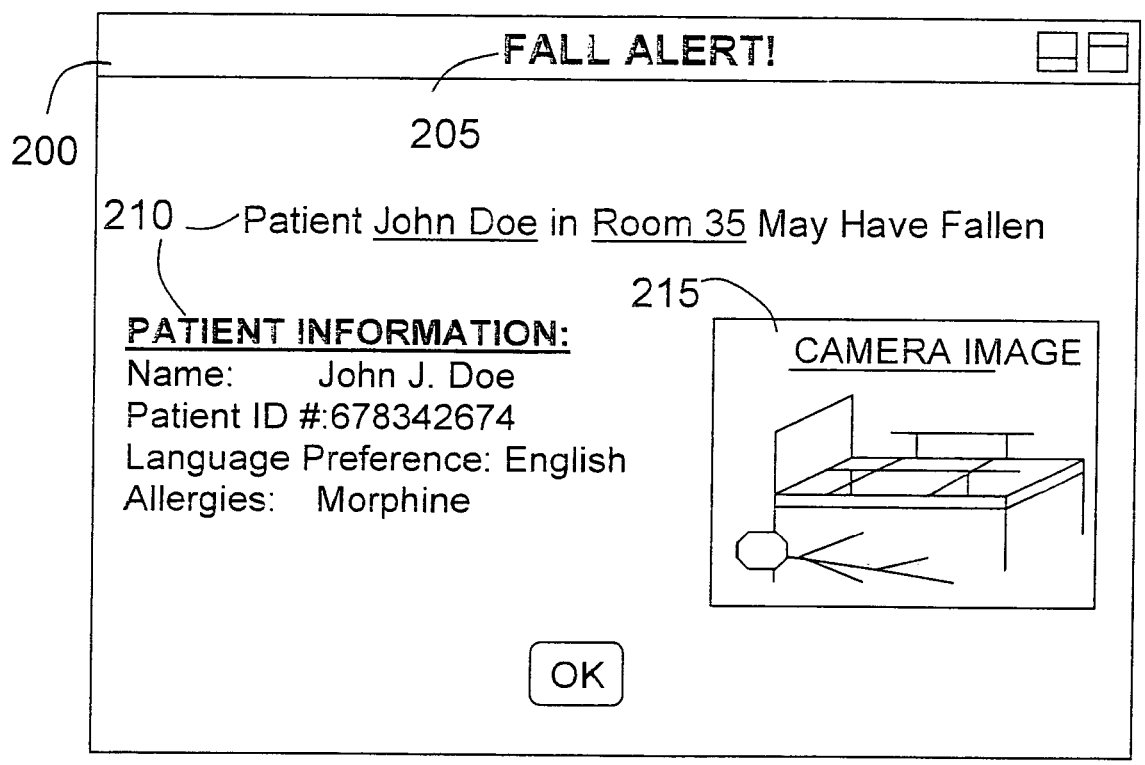
FIG. 2 illustrates an exemplary visual alert indicating that a patient may have fallen.

FIG. 2 illustrates an example of a visual alert that is a graphical display window containing an indicator that the patient may have fallen. In FIG. 2, an interface window 200 may be generated by a visual display. The interface window may contain textual information 205 that conveys that a patient has fallen. Also included in this exemplary interface window may be patient information 210, for example, information identifying the name of the patient, an alphanumeric identification assigned to the patient, the room number of the patient, the patient's preferred language and significant allergies. Although not shown, there may also be a generated map or floor plan of the facility and an indication of where the fallen patient is located. The exemplary fall alert of FIG. 2 may be presented on any peripheral visual display, or on any computer device having a visual display that is built into the computer device, for example a Personal Digital Assistant.

Cameras 140 may be mounted in the patient's room at locations that provide knee-level images of floor areas where falls are likely and RFID floor antennas are located. For example, a camera may be mounted along the front, lower edge of a nightstand to provide images of the floor area along one side of the bed. The same floor area next to the bed can be imaged by cameras mounted to the bed frame or to nearby walls. The knee-level camera image 215 may be presented on the Fall Alert display 200 to allow the attendants to quickly verify that a fall has occurred. For privacy reasons, the camera image can be highly distorted to make it impossible to identify any features of the facial, chest and groin areas.

Another exemplary action resulting in an alert that may be performed by the central monitoring computer 110 may be to control or communicate with peripheral devices 120 that are one or more audio speakers. As one of ordinary skill in the art would understand, a computer can communicate with a speaker, and the communications can contain commands, instructions, or information that result in the sounding of an auditory alert indicating that a patient may have fallen. The speaker(s) may sound out that a patient may have fallen, and may also sound out the location of the patient, for example, "Code Orange in Room 325". The speakers may be located in a hallway near the patient's room, where a nearby attendant may be more readily available to quickly attend to the fallen patient. The speaker(s) may be connected to the central monitoring computer 110 either by hard wire or wirelessly. The alert message may be repeated by the speaker(s) at predetermined, periodic intervals until the RFID floor antenna 100 detects the proximity of an attendant's badge or detects that the RFID fall tag 115 is no longer in close proximity to the floor.

As another example, the central monitoring computer 110 may perform an action resulting in the generation of an alert indicating that a patient may have fallen by transmitting a communication to one or more other computing devices 130. The communication may contain information or instructions. Such computing devices 130, which may have peripheral devices 135 coupled to them, can then perform one or more alert actions, for example as described above. In addition to displaying a visual alert, computing devices 130 capable of doing so may display a text message, sound an audible alert, or vibrate, so that an attendant may be informed of a possible fall condition.

In an exemplary embodiment, the central monitoring computer 110 receives periodic communications or keyboard inputs that tell the central monitoring computer 110 whom the responsible attendant (or attendants) is for each patient. An alert action can thus be directed to the computing device 130 of the responsible attendant for the patient that may have fallen. The central monitoring computer 110 may redirect communications to the computing device of an alternative attendant if the possible fall has not been acted upon within a predetermined period.

Once the indicator has been generated and conveyed to patient care staff, the patient care staff may investigate the possible fall. The time and other details about each alert may be conveyed to the charge nurse or other administrator at the beginning or end of each shift.

In another exemplary embodiment, the RFID transceiver circuit 105 may be programmed to, or operative to, perform one or more of the functions attributed to the central monitoring computer 110, as described above. For example, the RFID transceiver circuit may determine whether the tag 115 remains in proximity to the RFID antenna for a predetermined period; it may, if called for, determine whether the RFID tag 115 is an RFID fall tag; and it may perform any of the actions described in the above paragraphs. The RFID transceiver circuit 105 of this embodiment may be coupled with one or more computers and/or peripheral devices in a manner not unlike the system options described in the above paragraphs.

The knee-level camera 140 may also be used to aid in the detection of falls. The camera images may be analyzed to determine when a large object falls to the floor, i.e. downward motion of a large object that remains on the floor. This situation will be identified as a possible fall. When a fall is detected via the image analysis algorithm or by RFID floor antennas at the fall location, the camera image 215 of the floor area may be presented on the fall alert display 200. Most institutions will require each patient to pre-approve the use of knee-level cameras and to also specify the clarity of the displayed camera images 215. Using two redundant methods for detecting falls improves the accuracy of the fall detection scheme.

The camera images may be displayed on the peripheral device 120 associated with the central monitoring computer 110, wherein the peripheral device 120 may be a visual display. Although the use of a camera may be considered an encroachment of privacy by some patients, many patients who have a history of falling may want to be monitored by any and all means possible, and thus may pre-approve the use of cameras to confirm and display falls. An exemplary method includes determining whether a patient has a history of falls, asking a patient to pre-approve knee-level surveillance during the admissions process, and linking RFID tags associated with the patient to the patient's records. Optionally, the pre-approval step may involve asking a patient to specify pre-approved surveillance at a particular clarity level (e.g. fuzzy image or clearest possible resolution). The desired clarity of the video or snapshot images may be linked with the patient's record, and the patient's record can be used to adjust the resolution of the camera, or the resolution of the image captured by the knee-level camera. In an exemplary embodiment, a central monitoring computer 110 receives the image captured by the knee-level camera. It may cause a peripheral device 120 such as a visual display to generate the image, or it may transmit the image to one or more other computing devices 130 for display on a peripheral device 135 coupled to the one or more computing devices 130. In exemplary FIG. 2, the graphical display 200 displays not only an indicator 205 that a patient has fallen, but also the knee-level camera image 215.

Figure 3:
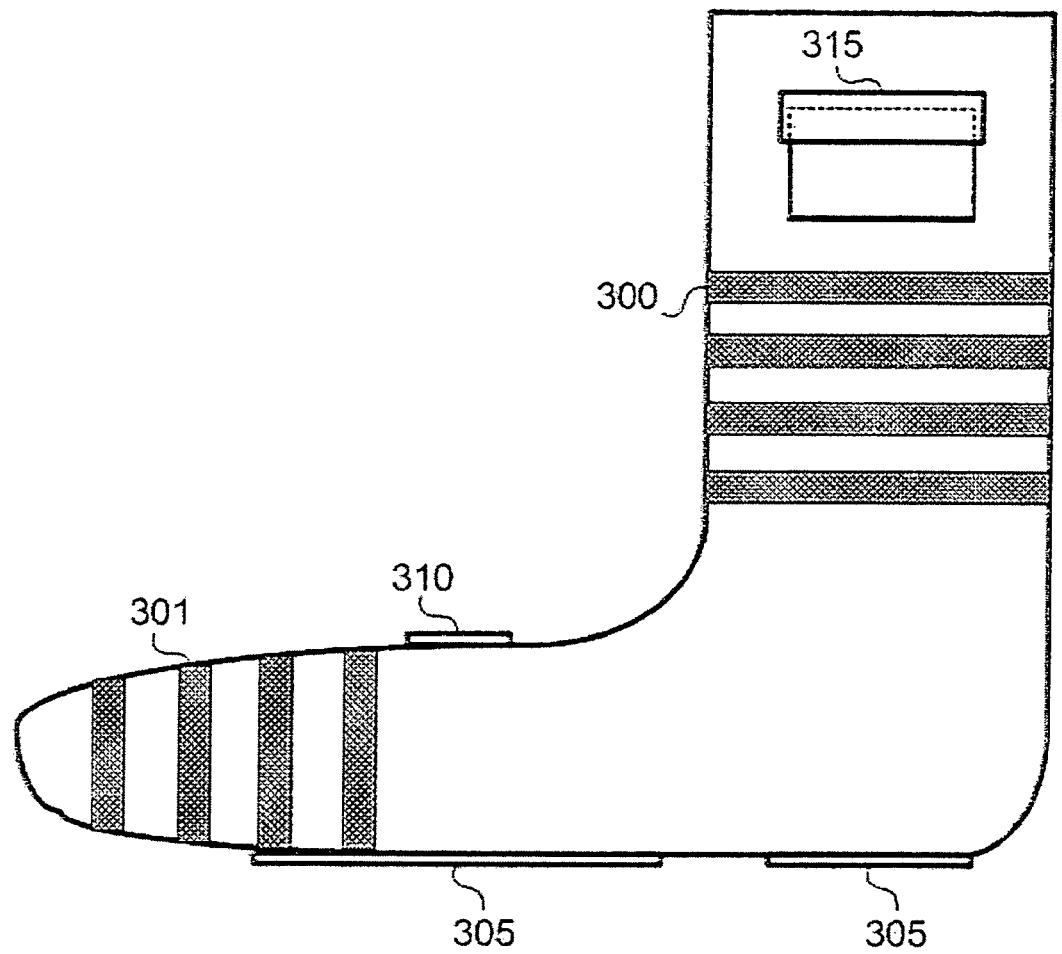
FIG. 3 illustrates an exemplary embodiment of a sock having RFID tags associated therewith.

The same knee-level camera may be also used to detect bed egress via a different pattern recognition algorithm, i.e. detecting when a sock with distinctive features comes off the edge of the mattress. The sock in FIG. 3 is exemplified with striped patterns 300 and 301 to make it easier to detect bed egress using a knee-level camera next to the bed and a pattern recognition algorithm that detects when the striped sock comes off the edge of the mattress. Hence, the same knee-level camera next to the bed may be used to detect falls, to detect bed egress and to also present a distorted image of the floor area next to the bed as a part of the fall alert display.

Detection of Patient Wandering RFID floor antennas 100, examples of which have been described above, may be also used to detect wandering. The same floor antennas can detect when a patient has wandered out of a room into an unauthorized area. For example, one or more RFID floor antennas 100 may be placed near a doorway, which may be the exit to the room. One RFID floor antenna 100 may be located near the outside edge of the doorway to detect when a patient is wandering into an unauthorized area, and another floor antenna may be located just inside the doorway to detect when the patient has returned to the authorized area.

A patient may wear an RFID tag on his or her ankle or foot. An RFID tag may be imbedded below the skin of the ankle or foot, such as a sub-dermal implant or a trans-dermal device, or attached to the skin using a biocompatible tape or adhesive. An RFID tag may be attached to an anklet worn by the patient, or a patient may wear a sock having an RFID tag associated therewith. One exemplary embodiment of such a sock is illustrated in FIG. 3. FIG. 3 presents a sock having RFID tags at locations 305, 310, or 315, wherein 305 may be associated with non-skid soles. Location 310 is along the upper portion of the sock, and location 315 is at the top edge of the sock. The pocket 315 may be stitched to the sock. The pocket may also have attached thereto a flap for enclosing an RFID tag, wherein three edges of the flap are attached to the pocket. The pocket may also have Velcro or one or more buttons for enclosing the RFID tag. The RFID tag at location 305, 310, or 315 may be attached to the sock by way of one or more buttons (including snap-on), a clip, adhesive, or Velcro.

Figure 4:
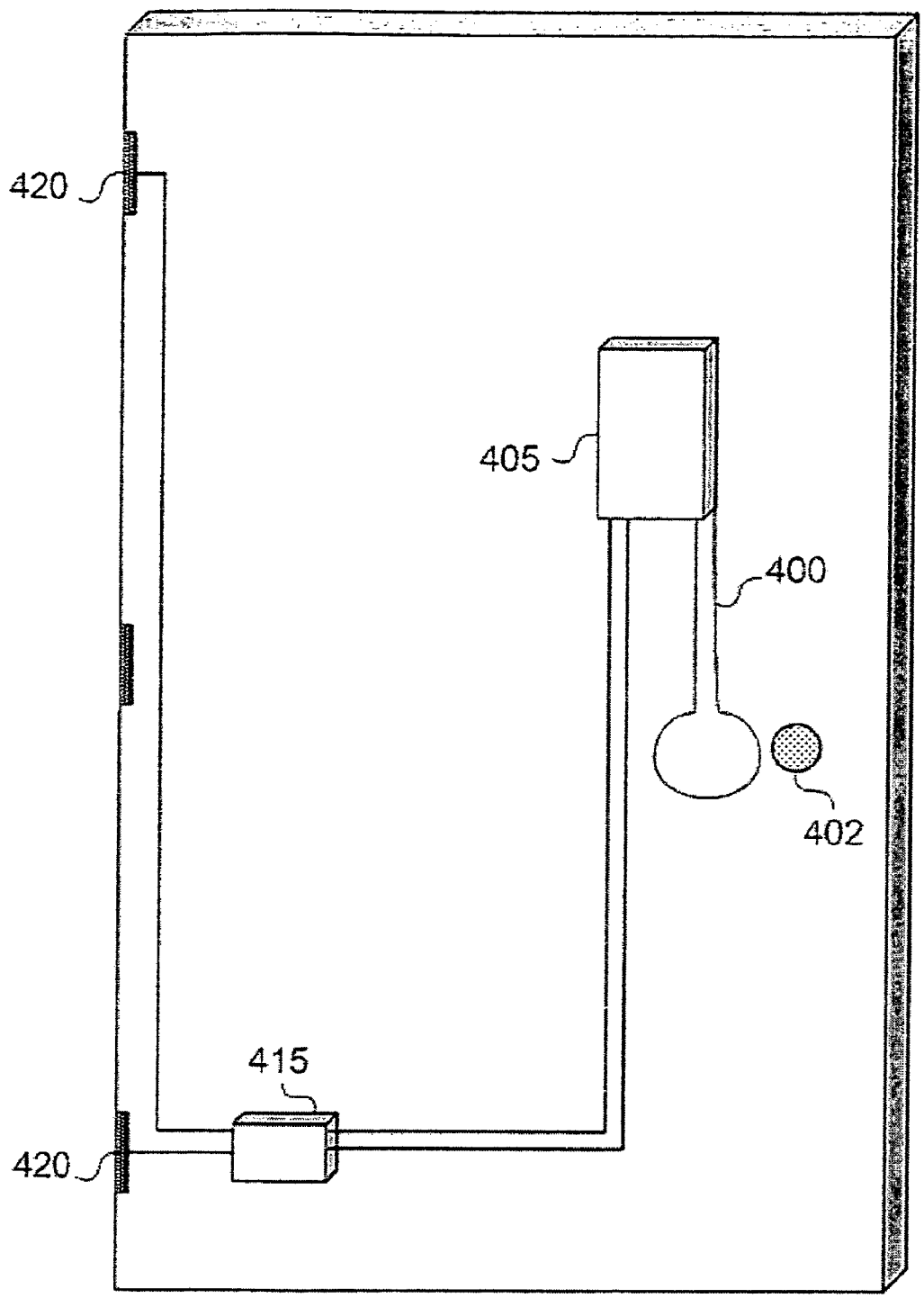
FIG. 4 illustrates an exemplary embodiment of an RFID door antenna.

If a lower body RFID tag comes within range of an RFID floor antenna 100, then the patient's RFID tag can be read, and wandering patients can be identified using the same or similar electronics described above for detecting falls via upper body RFID tags. It is also possible to detect wandering using the upper body RFID tags that are primarily used to detect falls. For example, RFID antennas may be disposed within a door, door jam, or adjacent wall to read the patient's upper body tag while passing through the doorway. In the exemplary embodiment shown in FIG. 4, an RFID antenna 400 is disposed within a door and positioned close to the doorknob 402. The RFID antenna 400 may be of any type known to those of ordinary skill. An RFID Transceiver circuit and other electronics 405 may reside within the door as depicted in FIG. 4 or may be mounted inside an adjacent wall or ceiling. The RFID transceiver circuit 405 is coupled to the RFID door antenna 400. Power to the RFID transceiver circuit 405 may be supplied by a battery 415. The battery 415 may be rechargeable and may be trickle charged by electrical current that flows through the door hinges 420 generated by a power supply (not shown) inside the wall or ceiling. As described in more detail below, when a patient having an RFID tag associated with his or her wrist reaches for the doorknob 402, the RFID door antenna 400 and RFID transceiver circuit 405 inside the door can be used to identify the patient and trigger an alert if the patient is unauthorized to pass through the doorway. It will be important for the patient to have an RFID tag on each wrist since the patient could use either hand to open the door. The communications between each RFID instrumented door and the Central Monitoring Computer 110 can be hardwired via the conductive hinges 420 or the communications can be wireless (e.g. 802.11a, b, or g).

Figure 5:
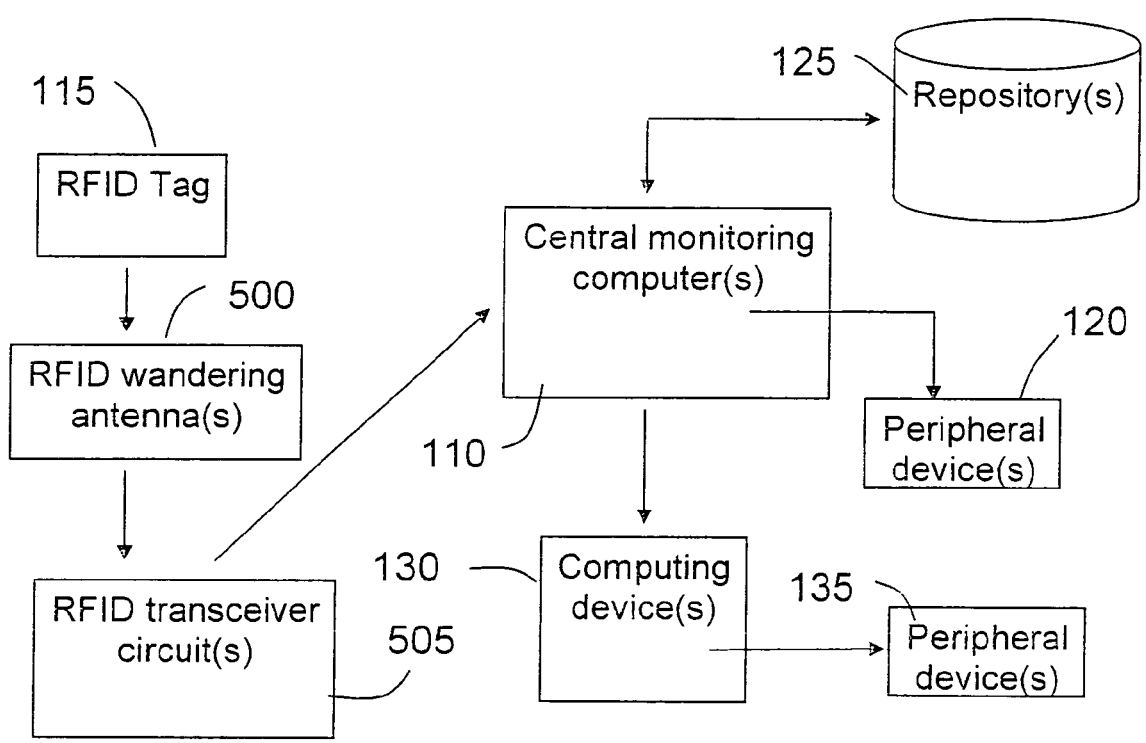
FIG. 5 is an illustration of an exemplary embodiment of a system that may be used to detect and alert of wandering using RFID technology.

FIG. 5 illustrates an exemplary embodiment of an RFID system that detects wandering. RFID floor antennas 100 and RFID door antennas 400 can be used to detect wandering and are collectively illustrated in FIG. 5 as element 500. The RFID transceiver circuit(s) 505 are interfaced to either RFID floor antenna(s) 100 or RFID door antennas 400, or both. It is possible to read one or more door antennas plus one or more nearby floor antennas using a single transceiver circuit using a multiplexer circuit. Hence, the RFID transceiver circuit 505 may also include special interface electronics and a multiplexer.

For example, one door antenna 400 could be located inside the door near the door knob or encircling the door knob, a second door antenna could be positioned inside the door jam or adjacent wall (not shown in any figure), a floor antenna could be located just inside the doorway and a second floor antenna could be located just outside the doorway (not shown in any figure). RFID transceiver circuits are much more expensive than RFID antennas; therefore, the above described four-antenna system can provide redundant detection of directional wandering at minimal cost.

FIG. 5 also depicts an exemplary RFID tag 115, which may be an upper body RFID tag as described above, or may be a lower body RFID tag associated with a patient's ankle or foot located in an ankle band or sock, such as RFID tag 305, 310 or 315.

The RFID Transceiver circuit 505 may be coupled or networked with one or more computers, which may be a central monitoring computer 110 as described above, or some other central monitoring computer(s). Such a central monitoring computer may be coupled as described above with one or more repositories, such as repository 125 as described above, peripheral devices, such as the peripheral devices 120 as described above, and other computing devices, such as computing devices 130 as described above. The computing devices may be coupled with peripheral device 135 or other computing devices (e.g. wireless Personal Digital Assistants).

For convenience and by way of illustration only, a method for detecting wandering will be described using an exemplary embodiment in which some of the same computing elements, such as central monitoring computer(s) 110, may be used to detect and alert of possible falls.

When an RFID tag 115 is in proximity to or comes close to an RFID wandering antenna 500, a signal transmitted by the RFID tag 115 (regardless of active or passive) is received by the RFID wandering antenna 500. Similar to what is described above with respect to fall detection, the proximity can be a range that is preset. The RFID transceiver circuit 505 coupled to the RFID wandering antenna 500 processes the signal received by the RFID wandering antenna 500 and communicates with a central monitoring computer 110. The signal originating from the RFID tag 115 may contain identification information such as a binary number or some other unique identifier. This identification information may be communicated to the central monitoring computer 110 by the RFID transceiver circuit 505. The communications between the Transceiver circuit 505 and the central monitoring computer 110 can be hard wired or wireless. The central monitoring computer 110 may then use the identification information to obtain patient information stored in a local or networked repository 125. The central computer 110 may do this, for example, by querying the repository 125.

The central monitoring computer 110 uses the identification information obtained from the RFID tag 115 to identify the patient, and relevant patient data may be then obtained from the repository 125 to determine whether the patient has any wandering limits. If the patient should not be present in the area in which the RFID wandering antenna 500 is located, an action may be performed resulting in the generation of an alert indicating that the patient is or may be wandering. For example, RFID tag 115 having identification number 27825 may be associated with the patient record for Jorge Gomez. Jorge Gomez's patient data in Repository 125 may indicate that he should not be authorized to be in an area outside of his room and his preferred language is Spanish. If the signal from the RFID tag 115 was received by an RFID wandering antenna 500 located outside of Mr. Smith's room, an action may be performed resulting in the generation of an alert indicating that the patient is wandering.

As with fall detection, an action resulting in the generation of an alert indicating that a patient either is or may be wandering may be performed by one or more computers, including a central monitoring computer 110.

Prior to performing an action resulting in the generation of an alert indicating that the patient is wandering, a first action may be performed in which an audible communication is generated instructing the patient to return to an area where the patient is authorized to be. The central monitoring computer 110 may be coupled with peripheral devices 120 that are one or more audio speakers within hearing range of each wandering antenna 500. In this embodiment of the invention, a prerecorded or synthesized verbal message in the patient's preferred language is generated by the speaker(s) located near the wandering antenna 500 that received the signal from the patient's RFID tag 115. The audible message instructs the patient to return to an area where the patient is authorized to be, e.g. "Please return to your room" stated in the patient's preferred language.

After performing this first action, the central monitoring computer 110 detects whether the patient has obeyed the audible warning. If one or more different RFID wandering antennas 500 located on the authorized side of the doorway detect the patient's RFID wandering tag, then the central monitoring computer 110 may conclude that the patient has complied with the first alert action and may either take no further action, or may generate a second verbal message in the patient's preferred language, e.g. "Thank you for returning to your authorized area". If the patient does not obey the first verbal message within a predetermined time limit, then an alert signal is communicated by the central monitoring computer 110 to one or more predetermined computing devices 130. Consecutively or alternatively, the alert signal may be conveyed to one or more peripheral devices 120.

In another exemplary method, a lookup table may be used to consult the history of the patient to decide, based on the vulnerability of the patient, whether to generate one verbal warning message or to repeat the verbal warning message several times at increasing amplitudes. Any hearing impairments can be noted with the other patient data, and volume adjustments can be made.

If the patient's RFID tag 115 signal continues to be received by the RFID wandering antenna 500 located at the entrance to an off-limits area or if the RFID tag 115 signal is detected by another wandering antenna 500 in the off-limits area, an alert action may be performed to notify attendants of the patient's wandering or unauthorized access. Such an alert action may be similar to any of the alert options described in the above paragraphs, but the alert condition is indicated to be a possible wandering situation. Additional information relating to the wandering detection may be also conveyed, e.g. the exact location of the most recent wandering antenna 500 that detected the patient's RFID wandering tag 115.

In another exemplary embodiment, the RFID transceiver circuit(s) 505 may include computer components that perform one or more of the functions attributed to the central monitoring computer(s) 110. The RFID transceiver circuit(s) 505 of this embodiment may be coupled with the repository 125, one or more computing devices 130, and/or peripheral devices 120 to perform any of the alert options described above. It is also possible to use the same RFID floor antenna(s) 100 and/or RFID transceiver circuit(s) 105 to detect both falls and wandering.

An exemplary embodiment for detecting wandering may also account for multiple patients that wander together into an area. In such a situation, multiple signals may be received simultaneously from different RFID tags 115. This may produce collisions between two or more RFID tag signals that make it impossible to decode the signals. To account for this scenario, RFID tags 115 may be designed to transmit signals with different time delays, or to transmit signals at different carrier frequencies. For example, all of the RFID tags can be designed to be energized when they receive an RFID signal at 134.20 KHz. The signal subsequently transmitted by one activated RFID tag can be at a carrier frequency 134.21 KHz and another nearby RFID tag can be designed to transmit its signal at a carrier frequency of 134.22 KHz. The combined signal received by the RFID antenna can be separated using a variety of filtering methods.

Alternatively, the RFID tags can be all designed to transmit at the same carrier frequency with incremental differences in the time delay between the time when each tag is activated and when the tag transmits it encoded signal. In this method for solving the multi-tag collision problem, it will be important to keep track of all of the RFID tags issued to patients to make sure that no two patients are issued RFID tags with the same or similar time delays that will cause the RFID tag signals to overlap in time.

The above two methods for avoiding multi-tag signal collisions is particularly useful when the carrier frequencies are at the low end of the spectrum, e.g. 134.2 KHz. At 13.56 MHz and higher approved RFID frequencies, other published and patented encoding methods are more effective in dealing with the collision problem.

Detection of Bed Egress and Room Egress

Figure 6:
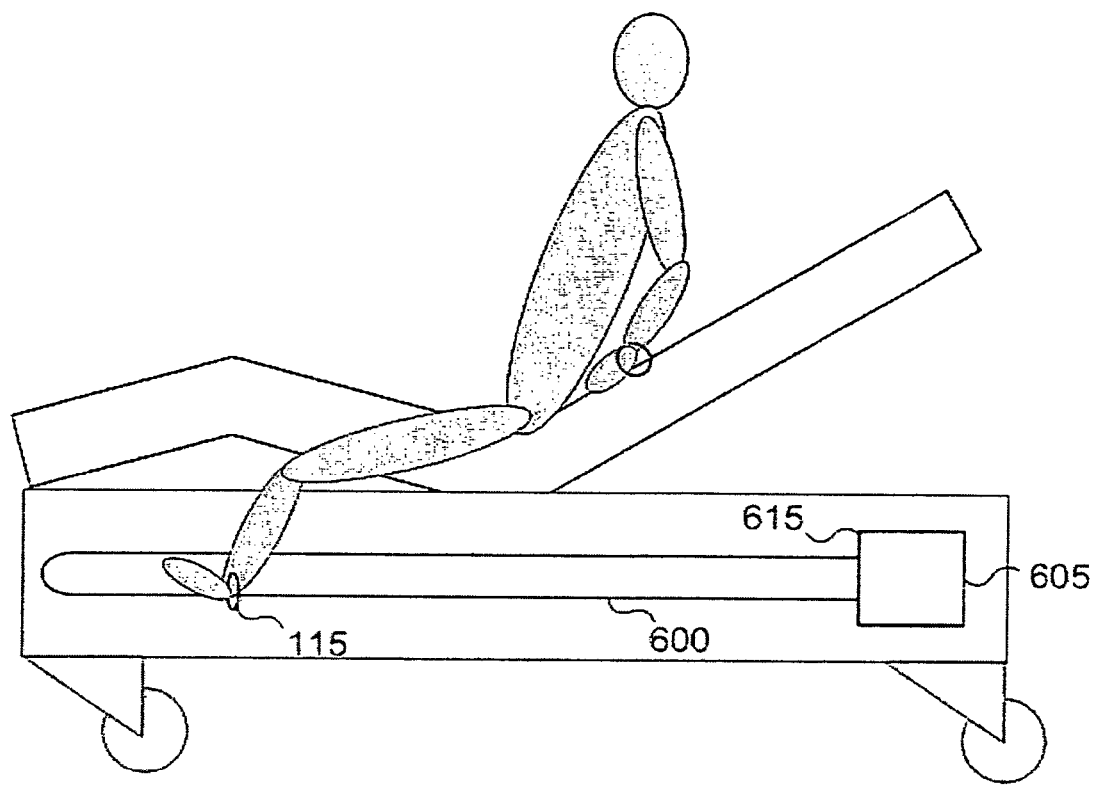
FIG. 6 illustrates an exemplary embodiment of a RFID bed frame antenna.

It is sometimes necessary for medical personnel to detect when a patient is attempting to get out of the bed, i.e. whether there is "bed egress". As shown in an exemplary embodiment in FIG. 6, one or more RFID antennas 600 may be disposed along one side of the bed frame, or preferably on all sides of the bed frame, including the foot end of the bed frame. The RFID bed frame antenna 600 may be coupled with an RFID transceiver circuit 605, which may be mounted inside an enclosure box 615. The enclosure box can be attached to the bed frame, to the wall, to the ceiling, or to an adjacent nightstand. A single transceiver circuit 605 can be connected to a multiplexer circuit to read several RFID antennas 600 in the bed and to also read one or more nearby floor antennas 100. RFID antennas along each side of the bed frame and at the foot end of the bed frame can be used to detect the proximity of an ankle or foot tag 115, and the proximity of an ankle or foot tag at these locations is identified as "bed egress".

If there any large openings in the bed frame supporting the mattress, then it may be possible for the bed frame antenna(s) 600 to read the patient's RFID tag(s) 115 while the patient is lying on the mattress. To prevent this error from occurring, a flexible metal foil or screen can be inserted inside the mattress or attached to the bed frame, shielding the patient from the bed frame antenna(s) 600 below the mattress. This shield may also improve the signal-to-noise of EKG, EEG and other electro-diagnostic measurements while the patient is lying on the mattress.

Figure 7:
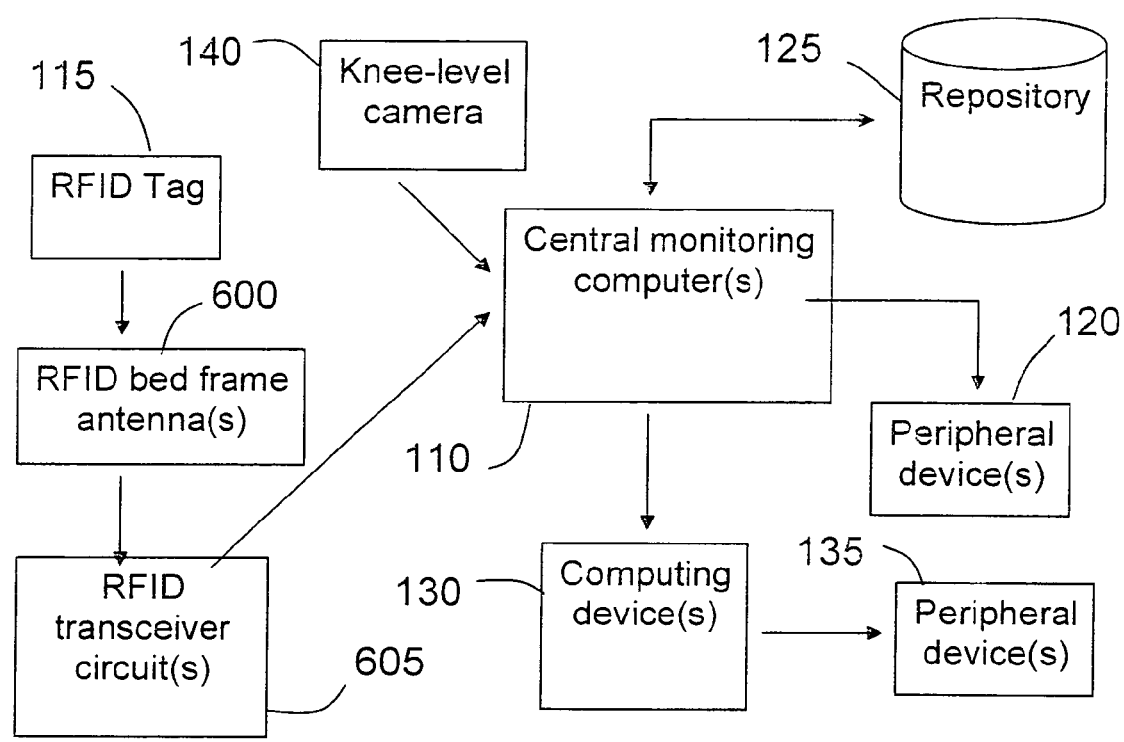
FIG. 7 illustrates an exemplary embodiment of a system that may be used to detect bed egress using RFID technology.

FIG. 7 depicts an exemplary RFID tag 115, which may be an RFID tag associated with a patient's foot or ankle, such as an anklet or a sock containing an RFID tag 305, 310 or 315. FIG. 7 also shows RFID transceiver circuit(s) 605 connected to one or more RFID bed frame antennas 600. The RFID transceiver circuit(s) 605 may include computer components, but a bedside computer (not shown in FIG. 7) may be used to analyze and record all of the incoming data, e.g. transceiver signals, camera images, EKG, etc. The transceiver circuit(s) 605 may be coupled or networked to a central monitoring computer 110, as shown in FIG. 7. Alternatively, the bedside computer described above may be used to collect the fall, wandering, egress and or other data for each patient, and the bedside computer could then communicate with the central monitoring computer(s) 110. The same bedside computer can also provide a variety of other communications, education and entertainment options to each patient. The central monitoring computer(s) 110 may be coupled with one or more repositories 125, one or more peripheral devices 120, and/or one or more other computing devices 130, e.g. wireless Personal Digital Assistants. It is likely that the same computer hardware 110, 120, 125, 130 and/or 135 will be used to detect, alert, and respond to falls, wandering, and bed egress at each institution.

FIG. 7 exemplifies one of many possible configurations of a bed egress detection system. Whenever an RFID tag 115 comes within range of an RFID bed frame antenna 600, the patient's RFID tag 115 can be read by the bed frame antenna 600. The read range can be adjusted up to a limit that depends on the RFID frequency, the RFID tag design, the antenna design, and the transceiver circuit design. The same range limits apply to the other RFID methods for detecting falls and wandering. The RFID transceiver circuit 605 is connected to the RFID bed frame antenna 600. The transceiver circuit 605 processes the encoded signal received from the RFID tag 115 and communicates with the central monitoring computer(s) 110. As described above, a bedside computer (not shown in FIG. 7) may be added to the system, interfacing between the collection of transceiver circuit(s) 105, 505, and 605 in each room and the central monitoring computer(s) 110. The same bedside computer can be also used to monitor EKG, EEG and other electro-diagnostic signals, plus provide communications, education and entertainment options, as described in the previous paragraph.

The signal originating from the RFID tag 115 may contain identification information such as a binary number or some other unique identifier. This identification information may be transmitted to the central monitoring computer(s) 110. The central monitoring computer(s) 110 may then use the patient identification information to obtain patient information stored in a local or networked repository 125, e.g. prior orders for "electronic bed restraint" and the patient's preferred language. If the central monitoring computer(s) 110 determines, based on the identification information obtained from the RFID tag 115 and the patient's repository records, that the patient should be confined to the bed, the central monitoring computer(s) 110 may then perform an action resulting in the generation of an alert indicating that the patient has gotten out of bed, similar to the actions described above, but to alert of bed egress instead of a possible fall. As with fall detection and wandering, a first computer, a second computer, and/or other computers down a communication chain, may perform the action resulting in the generation of an alert indicating that the patient has gotten out of bed.

The central monitoring computer 110 may be coupled directly, or through a bedside computer, to one or more speakers in the patient's room. Prior to performing an action resulting in the generation of an alert indicating that the patient has gotten out of bed, a prerecorded or synthesized verbal message in the patient's preferred language may be generated instructing the patient to remain in the bed, e.g. "Please remain in the bed." The volume level of the verbal message can be automatically increased if any auditory deficits are noted in the repository records for the identified patient. This audible communication may prevent a possible fall or wandering.

As with wandering, a lookup table may be used to determine, based on the vulnerability of the patient, whether to issue one verbal warning or two warnings. If after a specified period of time, a subsequent signal is still received by the RFID bed frame antenna 600, or has been received by an RFID floor antenna 100 near the patient's bed, then the central monitoring computer 110 can perform an action resulting in the generation of an alert indicating that the patient has gotten out of bed, the action being similar to that described above.

In another embodiment (not shown), a mattress may have one or more RFID antennas disposed within the mattress. The RFID mattress antennas may be coupled to one or more RFID transceiver circuits 605, which are also used to detect bed egress. Alternatively, the mattress can be assembled with its own transceiver circuit inside or near the mattress. When a mattress antenna at the foot-end of the mattress is no longer able to read a patient's foot or ankle tag, the transceiver circuit may then conclude that the patient's legs have moved off of the mattress. Prior to performing an action resulting in the generation of an alert indicating that the patient has gotten out of bed, a verbal warning message may be generated in the patient's preferred language at an appropriate volume level, as previously described.

The metal shield described above should be positioned under the mattress antennas, e.g. along the entire bottom surface of the mattress. The mattress antennas can be positioned between two layers of foam inside the mattress or imbedded inside the foam. Heating of the foam must be considered since long-range detection of RFID tags will require high current levels in the mattress antennas.

In each of the above described RFID methods for detecting falls, wandering and bed egress, the transceiver circuit(s) 105, 405, 505, or 605 may include computer components that are programmed to, or operative to, perform one or more of the functions attributed to the central monitoring computer 110. In these simpler and lower cost embodiments of the invention, the transceiver circuits may be directly coupled with the repository 125, computing devices 130, and/or peripheral devices 120.

The mattress antenna(s) described above can be also used to read the patient's RFID tag(s) 115 during medication deliveries to verify that the patient is receiving the correct medication(s). In this embodiment, a barcode reader can be connected to the bedside computer described above to read barcode labels on medications. The bedside computer can read the patient's RFID tag(s) 115 and the barcode label on each medication. The bedside computer can then communicate this information to the central monitoring computer 110. The central monitoring computer 110 can access the medication records 125 for each patient to determine when the identified patient is receiving an incorrect medication or dosage. Each medication error can be reported to the bedside attendant using a small LCD monitor on the barcode reader or by generating a verbal message using the same speaker that is used to prevent bed egress. The central monitoring computer 110 can also determine when a medication is late and can send an alarm code to the appropriate computer device(s) 130 or peripheral device(s) 120.

The mattress antenna(s) can be also used to read an attendant's RFID badge while standing close to the bed to determine the time when the identified attendant has responded to a nurse call. If the bedside computer also provides nurse call communications between the patient and the nurses' station, then the bedside computer can record the response times for each attendant and can convey this information to a supervisor's computer at the beginning or end of each shift.

A knee-level camera 140 can be positioned next to the bed, as described above. This camera has already been described as a device that can be used to detect falls next to the bed and to also display distorted images 215 of the floor area next to the bed when a fall has been detected in this area. The same camera can be also used to detect bed egress by detecting when the patient's foot comes within view of the knee-level camera 140. In a preferred embodiment of this invention, the patient is fitted with socks having non-skid soles and distinctive patterns and/or colors on the surface of each sock. FIG. 3 exemplifies this concept using a distinctive pattern of stripes 300 and 301, which could be alternating red and green stripes. The knee-level camera 140 images can be analyzed to recognize the distinctive pattern and/or colors printed on the sock to detect when the sock passes beyond the edge of the mattress and comes within view of the knee-level camera. The appearance of the sock is interpreted as an early stage of bed egress. The position and orientation of the knee-level camera 140 must be selected to make it impossible to see any part of the patient while lying in the bed. This positioning of the camera 140 insures that the patient's privacy will not be violated while the patient is lying on the bed.

When bed egress is detected via the knee-level camera 140, the same verbal message can be generated as when an RFID bed frame antenna 600 detects the egress, i.e. generating a verbal warning in the patient's preferred language and at an appropriate volume level. If the patient does not return both feet to the top surface of the mattress, the same methods can be used to alert the attendants as previously described. The knee-level camera 140 and mattress antenna detect an early stage of bed egress. The side antenna 600 and the floor antenna 100 next to the bed detect a late stage of bed egress. Some institutions may prefer a different sequence of actions when "Late Bed Egress" is detected. The redundant methods for detecting bed egress improve the accuracy of the detection scheme.

It should be evident to anyone with ordinary skill in the art that an RFID lower body tag and an RFID upper body tag can be identical accept for having different binary codes associated with each tag. It is also possible to use a combination of active and passive tags or to use a combination of passive tags that operate at different frequencies. For example, longer-range active tags can be used to detect wandering and shorter-range passive tags can be used to detect falls and bed egress. The active and passive tags can operate at different frequencies to reduce the likelihood of interference problems.

Embodiments of RFID Floor Antennas

Figure 8:
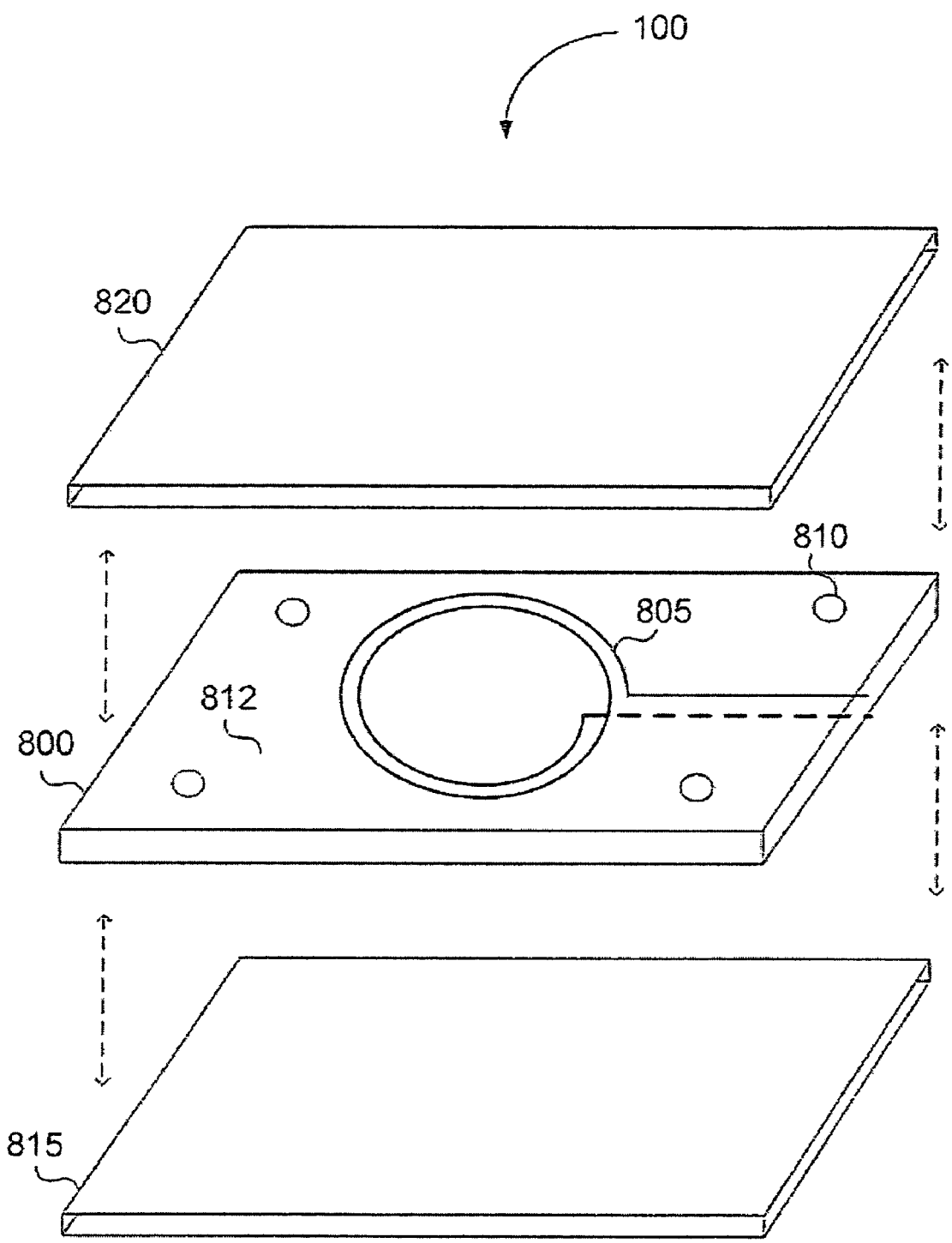
FIGS. 8-13 illustrate exemplary embodiments of RFID floor antennas.

Falls are detected when an upper body RFID tag 115 remains within range of an RFID floor antenna 100 for a predetermined period of time. One exemplary embodiment of an RFID floor antenna 100 is illustrated in FIG. 8. In this embodiment, any RFID antenna 805 printed on a flexible circuit board 800 known to those of ordinary skill may be used. Large perforations 810 may be made where the RFID antenna 805 is not printed. The printed circuit board 800 may then be attached via an adhesive 812 to a backing material 815 and to the top surface of the floor covering 820. The top surface of the floor covering 820 may be any flooring material including carpet, linoleum, vinyl, fiber reinforced vinyl, plastic, wood, laminated wood, ceramic tile, porcelain tile, granite or marble. The backing material 815 may be any durable nonconductive material, including but not limited to jute, foam, non-woven polymers, or woven polymers. The printed circuit board may be perforated with holes 810, and the opposing surfaces may be sanded, sandblasted, and/or etched to increase the surface area and improve the bonding with the adhesive. The printed circuit board 800 may be printed on both side, as depicted in FIG. 8, or the printed circuit may be contained on one side of the circuit board with a separate insulated wire attached to the circuit that jumps over the spots where the printed circuit lines would otherwise intersect. In other similar embodiments, the printed circuit board 800 may be imbedded inside the backing material 815, or the printed circuit board may be attached to the bottom surface of the backing material 815 using the adhesive 812.

Because current printed circuit boards may not be able to withstand the stresses placed upon hospital floors, padding may also be used. The padding layer may contain one or more components of polyurethane, polyethylene, polystyrene, rubber, latex, foam, or any other type of cushioning material known to those of ordinary skill. The padding layer may also be reinforced by polymer fibers mixed with one or more of the cushioning components described in the preceding sentence. The padding layer may be used as the backing material 815, or it may be inserted above the printed circuit board 800 as a separate layer not shown in FIG. 8.

The conductive antenna circuit forming the RFID antenna may be printed onto the flooring sections, floor tiles, carpet backing, carpet pad or a polymer fabric that is attached to or laid down next to any of these flooring components. For example, metal RFID antenna(s) can be imbedded inside the padding material, and the padding material can then become layer 800 in FIG. 8. The backing material 815 may be a polymer fabric or any other backing material commonly used to reinforce floor coverings. In some applications, the backing material 815 may be eliminated, leaving only layers 800 and 820 in FIG. 8.

In another embodiment, the backing material 815 may be attached directly to the bottom surface of the top layer 820, and the padding material 800 containing the RFID antenna(s) becomes the bottom layer in FIG. 8, that is layers 800 and 815 are switched.

In another embodiment, the antenna circuit may be printed onto one or both surfaces of a polymer fabric using a conductive ink, a metallic (conductive) paint, or an evaporative coating of metal. The evaporative coating of metal may be applied using a template that prevents the metal from attaching to parts of the fabric surface, or the coating may be applied to the entire surface and then photo-etched using known PC Board techniques. To increase the conductivity, the printed circuit lines created by the ink, paint, or metal coating may be electroplated. The printed polymer fabric may be positioned at either the middle or bottom layer in FIG. 8. If a spiral antenna circuit is printed on only the top surface of the polymer fabric, then electrical wires will need to be attached to the printed circuit to jump over the points where the circuit leads intersect. If the intersections are avoided by also printing circuit lines on the bottom surface of the fabric, then the circuit will be much better protected when positioned at the middle layer 800, as depicted in FIG. 8. The connections between the top and bottom circuit lines can be achieved using small metal rivets. In some applications, if the printed polymer fabric becomes layer 800, then it may be possible to eliminate the backing material 815.

In the embodiment described in the preceding paragraph, conductive threads may be used as an alternative method for imprinting an antenna circuit onto a polymer fabric. The conductive threads may be used on the lower bobbin of a sewing machine. If portions of the antenna circuit are stitched onto both surfaces of the polymer fabric, then required electrical connection(s) between the two surfaces may be achieved using small metal rivets, as described in the preceding paragraph. The conductivity may be increased by using a large number of intersecting conductive threads for each loop of the antenna. Another advantage of using intersecting conductive threads is that the antenna will continue to function when a single thread is broken.

In another embodiment of the invention, the padding material and RFID antenna(s) are parts of an underlayment, which is installed before a conventional floor covering is installed. The padding may contain one or more components of polyurethane, polyethylene, polystyrene, polystyrene foam, rubber, or any other type of cushioning material known to those of ordinary skill. The RFID antenna(s) may be imbedded inside or attached to the padding, as described above. Alternatively, the antenna(s) may be printed, painted, evaporative coated, or stitched onto a polymer fabric, as previously described. The printed fabric can be then attached to the top or bottom surface of the padding.

Figure 9:
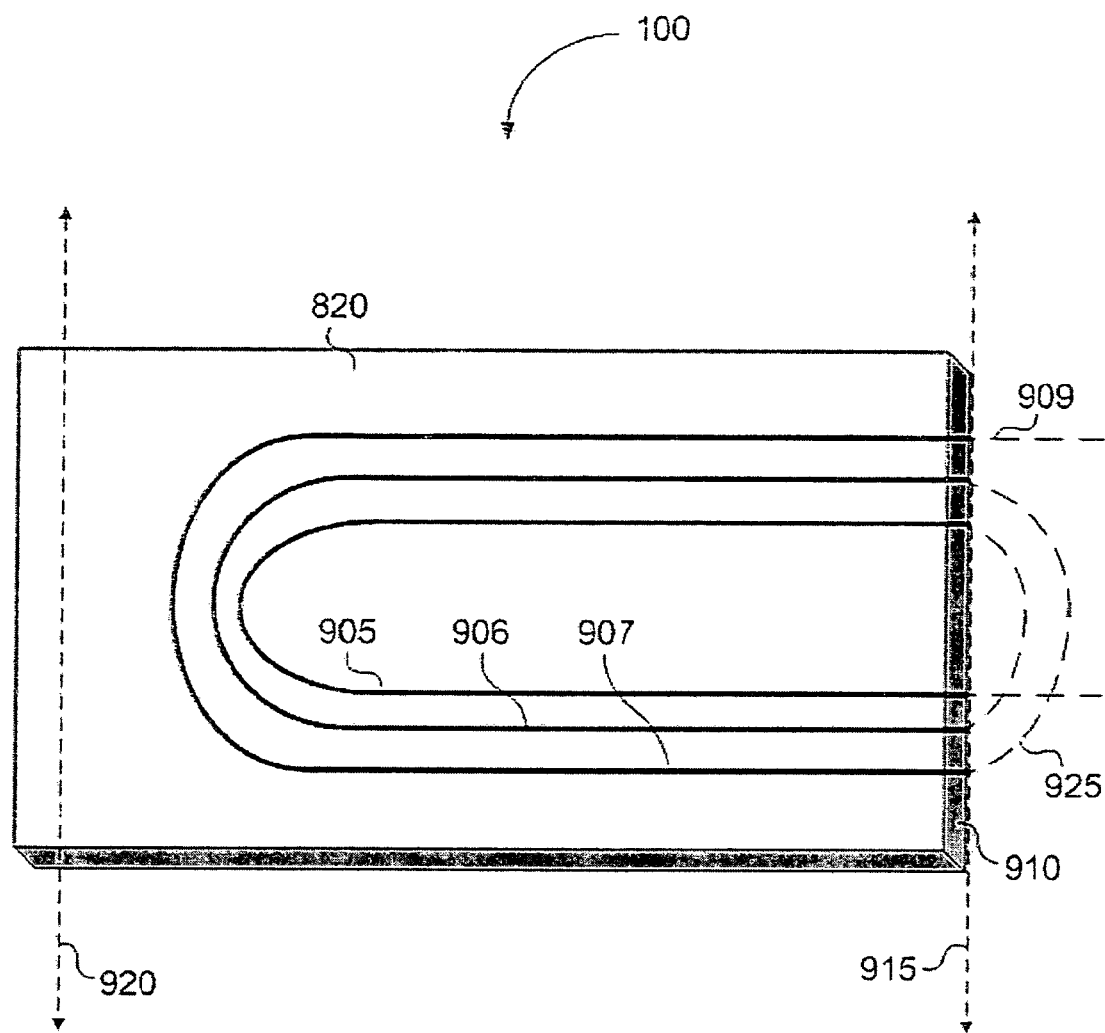

A more practical design of an RFID floor antenna 100 is depicted in FIG. 9. In FIG. 9, conductive leads 905, 906, and 907 are attached to the top layer 820 of the floor covering. The material used to create the U-shaped elements 905, 906, 907 can be any conductive material described above. The U-shaped leads can be also created using metal foil, electrical wire, or metal mesh screen. The conductive material is cut into a pattern resembling elongated U's, as depicted in FIG. 9. In the exemplary embodiment illustrated in FIG. 9, the conductive material 905, 906, and 907 form three U-shaped antennas. Other embodiments may have a different number of U-shaped loops formed by the conductive material. The number of U's shaped loops determines the number of loops in the spiral antenna, which is created by interconnecting the ends of the U's using electrical wires 925. More or less than three loops of conductive material may be used, depending on the desired antenna impedance, range, and other factors. The conductive material 905, 906, 907 may be affixed via any type of adhesive known to those of ordinary skill in the art to the bottom surface of the flooring material 820. The ends of each U can be connected to a circuit board which contains the interconnections 925 and a transceiver circuit 105.

Metal mesh screen is particularly effective as the conductive material used to create the U-shaped leads 905, 906, and 907 exemplified in FIG. 9. At high frequencies, the electrical current primarily flows (i.e. electrons pass from atom to atom) along the surface of the conductive medium. Hence, the large surface area contained in a metal screen has an advantage of providing lower resistance at higher frequencies. Another advantage of metal screen is that the screen can be attached to or imbedded inside flooring materials more securely. Some of the different attachment and imbedding options are described below. When using metal screen as the conductive material for each of the U-shaped leads, it is also advantageous to make the resistance along each U-shaped lead the same by making the outer U-shaped leads 906 and 907 wider.

Figure 10:
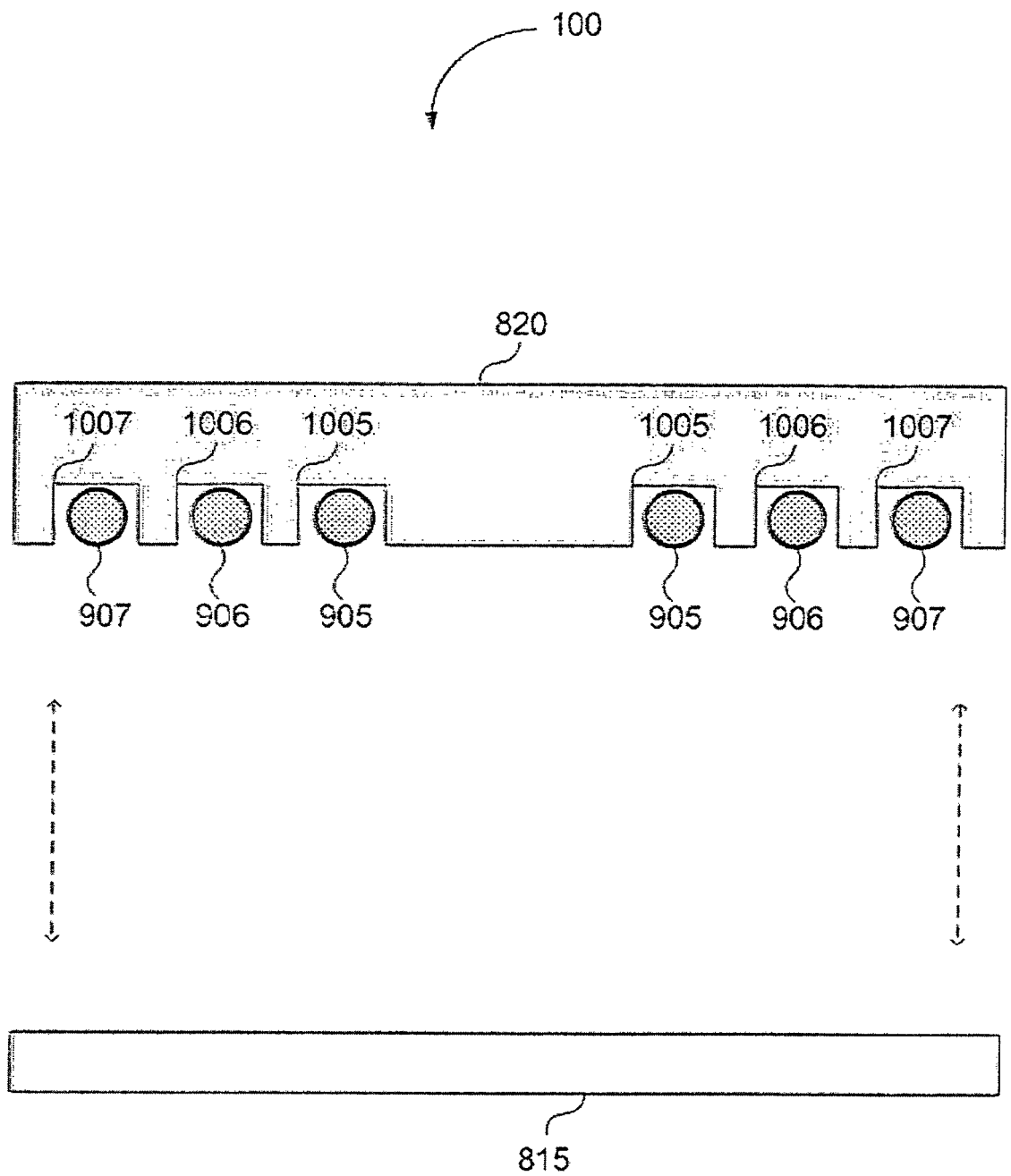

A further embodiment of an RFID floor antenna 100 is depicted in FIG. 10, which is a cross-sectional view. In this embodiment, instead of being attached directly to the bottom of layer 820, the conductive materials 905, 906 and 907 are contained inside grooves 1005, 1006, and 1007. The grooves 1005, 1006, and 1007 may be made by cutting, molding, etching, or pressing the conductive leads 905, 906, and 907 into the undersurface of the flooring covering 820. The grooves may take on any shape, including a square shape as depicted in FIG. 10, or a rounded shape (not shown). A square shaped groove would be most appropriate when using flat metal screen as the conductive material. Adhesives or filler materials may be applied to the grooves to keep the conductive material 905, 906, and 907 enclosed within the grooves 1005, 1006, and 1007. Although not necessary, a backing material 815 may then be attached to the undersurface of the flooring material 820 to enclose the conductive materials 905, 906, and 907. In a similar embodiment, after the grooves are made, conductive material in a liquid form such as molten metal or conductive metallic paint may be poured into each groove. The conductivity may be increased by electroplating the exposed surface of the conductive material with a highly conductive metal.

In other embodiments, the U-shaped leads 905, 906, and 907 can be attached, imbedded, printed, painted, evaporative coated, or stitched onto one layer of a flooring product, using methods described above. The disclosure above describes how the U-shaped leads 905, 906, and 907 can be printed, painted, evaporative coated, or stitched onto a polymer fabric, which becomes a layer of the flooring product or alternatively becomes a layer of a foam underlayment product. The underlayment product can be installed and tested before the flooring product is installed. The two main advantages for using U-shaped antenna leads are that the leads do not cross, and the concentric U's can be cut along their open ends to reduce the length of a prefabricated floor covering. The latter advantage is particularly important in wall-to-wall applications.

In another embodiment, metal wire, metal foil, or metal screen can be cut to form U-shaped leads exemplified by 905, 906, and 907. The metal leads can be then attached to the top surface of a backing material 815 using an adhesive. The hard metal leads may be then pressed into a floor covering 820 that is deformable, such as uncured linoleum. In a similar embodiment, a flooring material that is moldable may be poured over the metal U-shaped leads and backing material.

Figure 11:
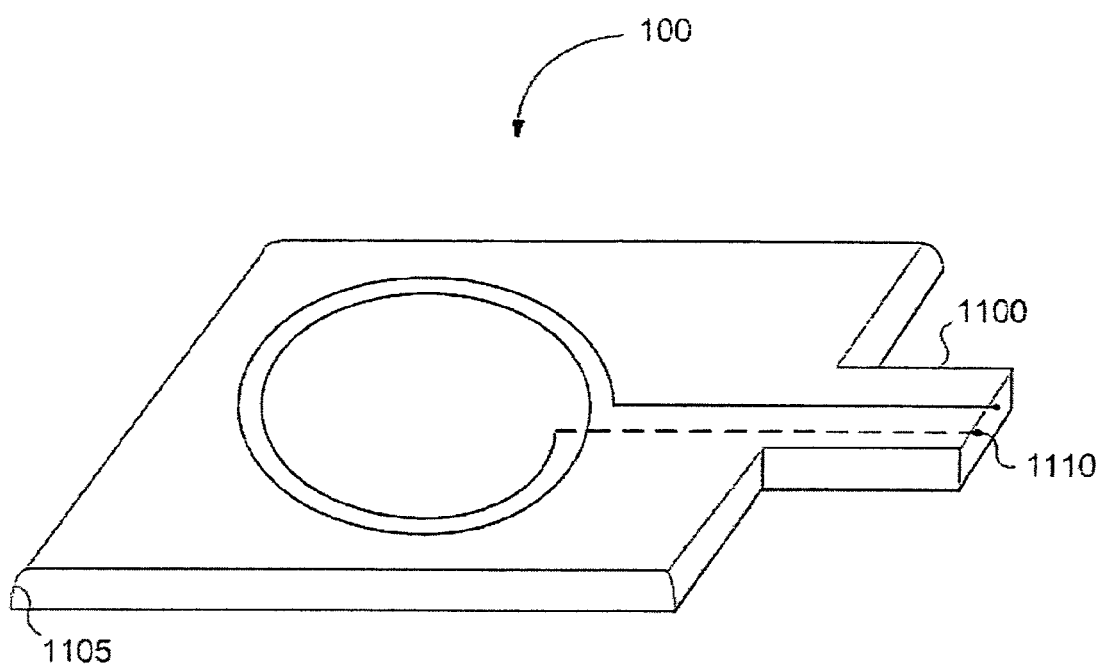

It is possible for one or more of the above discussed embodiments of an RFID floor antenna 100 to take on the form of a mat. FIG. 11 is an illustration of an exemplary RFID antenna 100 comprising a floor mat. The floor mat may have a protruded portion 1100 having conductive leads continuous with or connecting to one or more RFID antennas disposed within the floor mat. The edges of the floor mat 1105 may be tapered and reinforced with a stiffener material. The top surface of the mat may be rough or carpeted to increase the static and kinetic coefficients of friction, and the center section of the mat can be more padded and compressible to absorb some of the impact energy when a fall occurs. Two-sided adhesive tape may be stuck to each bottom edge of the floor mat to secure the mat to the floor. Alternatively, the floor mat may be secured to the floor using Velcro or suction cups. Each floor mat can be positioned near a wall, and the protruded portion 1100 with conductive leads 1110 can be connected to a special female receptacle providing an electrical connection to an RFID transceiver circuit 105 inside the wall. To further increase the accuracy for detecting falls, an array of force or compression sensors may be imbedded into the mat to detect when a large continuous object is lying on the mat, as opposed to several disconnected feet standing on the mat. The bottom surface of the mat may be covered by a non-skid, waterproof material.

Figure 12:
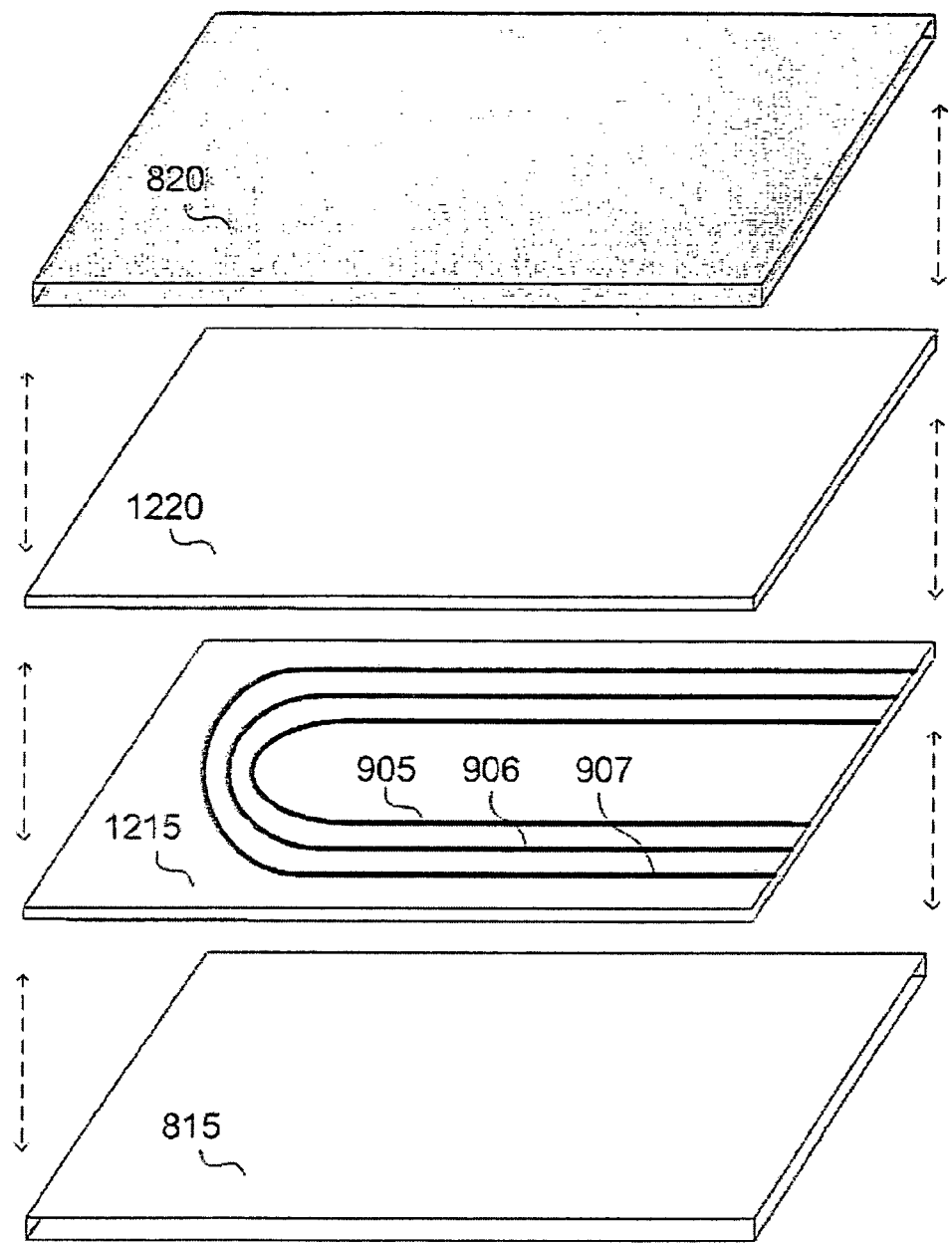

FIG. 12 is an illustration of another exemplary embodiment of an RFID antenna 100 whereby the conductive material forming the RFID antennas 905, 906, and 907 may be disposed between two deformable layers of padding 1215 and 1220. Each padding layer may contain one or more components of polyurethane, polyethylene, polystyrene, polystyrene foam, rubber, latex, or any other type of cushioning material known to those of ordinary skill. Metal foil or metal screen can be cut to form U-shaped leads 905, 906, and 907, and the U-shaped leads can be attached between the two layers of padding 1215 and 1220 using an adhesive or heating process. In an alterative embodiment, the U-shaped leads may be printed, painted, evaporative coated, or stitched onto a fabric, and the fabric may be then disposed between the two padding layers 1215 and 1220 using an adhesive or heating process. If the backing material 815 is needed, it may be attached to the bottom surface of the lower padding material 1215. The floor covering 820 can be attached to the upper surface of the top padding layer 1220.

Figure 13:
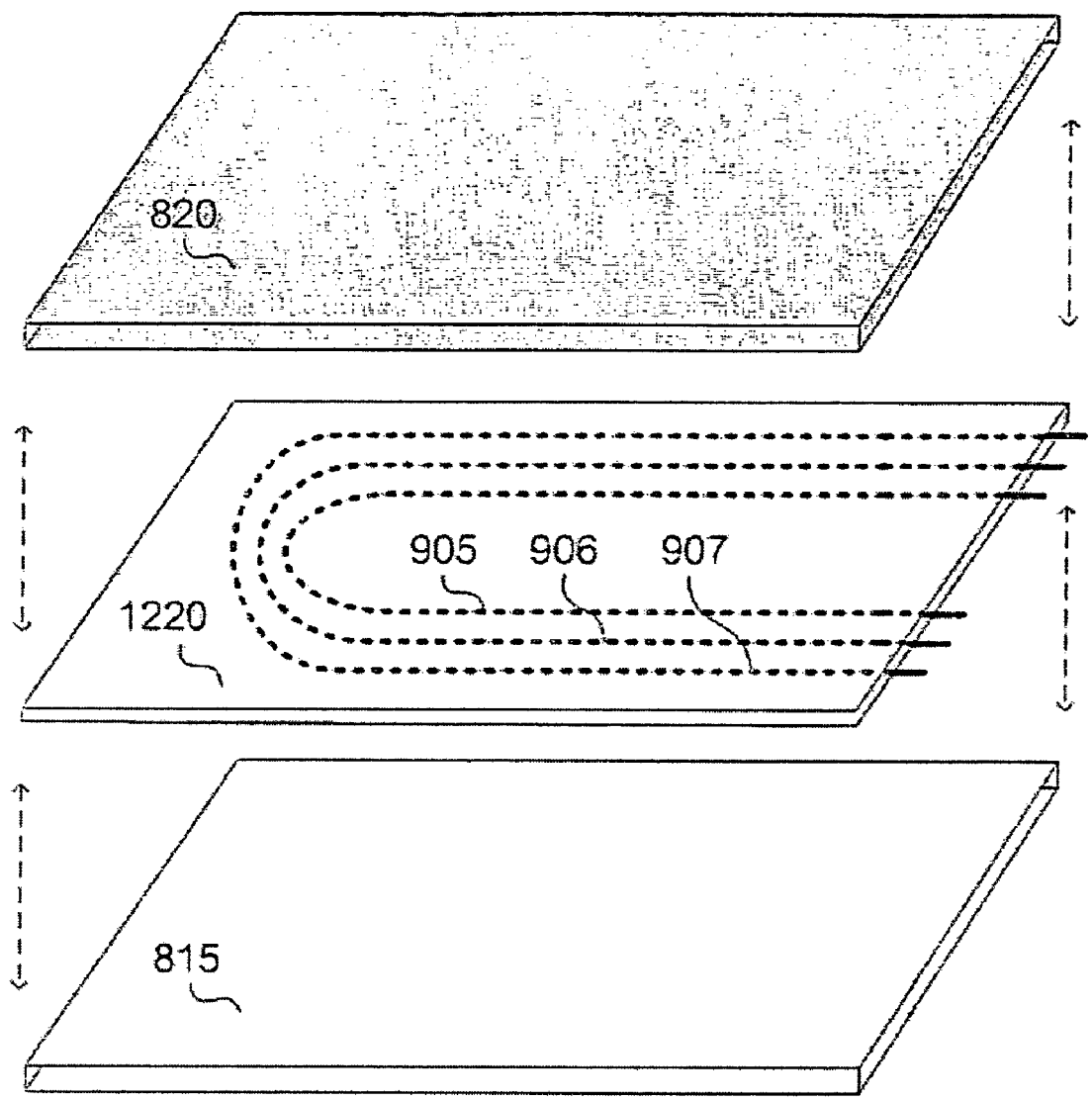

In an alternative embodiment shown in FIG. 13, U-shaped electrical wire, metal foil, or metal screen may be imbedded inside a single layer of padding 1220. The padding 1220 can then be disposed between the backing material 815 and the floor covering 820. In some applications, the backing material 815 may be eliminated. In a similar embodiment, the conductive leads 905, 906, and 907 may be affixed to a fabric, cloth, or gauze material first, before being imbedded inside the padding layer 1220.

In another exemplary embodiment, conductive material 905, 906, and 907 forming the RFID antenna may be affixed to a fabric, cloth, or gauze material, which is then adhered directly to the floor. After being adhered to the floor, an installer may cover the floor and RFID antenna with any type of floor covering, backing material, padding, underlayment, or cushioning material, including but not limited to those described above.

For all the embodiments of the U-shaped antenna design described above, it is possible to cut along the open ends of the U's to make the prefabricated floor covering fit the room dimensions. As depicted in FIG. 9, an installer can cut the prefabricated floor covering along line 915 using a knife. When line 915 is moved to the left in FIG. 9, the open ends of the U's can still be connected to the transceiver circuit board, and the interconnections 925 will create a spiral antenna. The installer may also trim the other end of the prefabricated floor covering without cutting any of the antenna loops, as exemplified by line 920.

Circuit Board for Floor Antennas

The open ends of the conductive U's (905, 906, and 907 in FIG. 9) must be connected to a transceiver circuit 105 which may reside on a circuit board. The circuit board can provide the electrical connections 909 and 925 to create a spiral antenna. In an exemplary embodiment illustrated in FIG. 14A, the circuit board 105 is mounted inside an enclosure box 1405 with sliding flanges 1410 at the top and bottom of the enclosure box 1405, similar to the design of some 110 Volt receptacle boxes. The screws 1415 at the top and bottom of the enclosure box 1405 pull on the sliding flanges 1410 and pinch the drywall 1420 to rigidly support the enclosure box 1405 inside the wall.

Figure 14A:
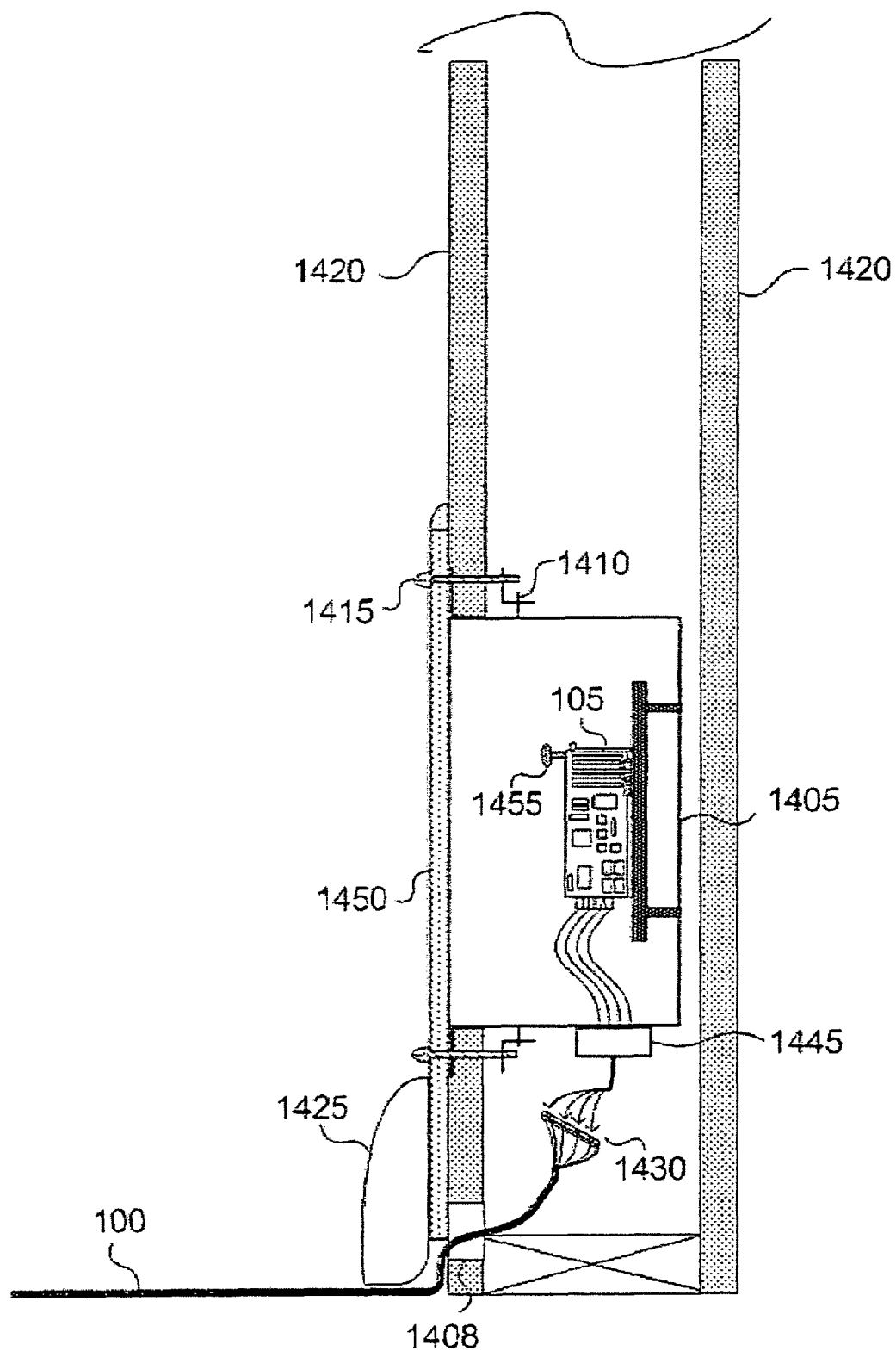
FIGS. 14A-14C illustrate an exemplary embodiment of an RFID Transceiver circuit disposed within a wall.
Figure 14B:
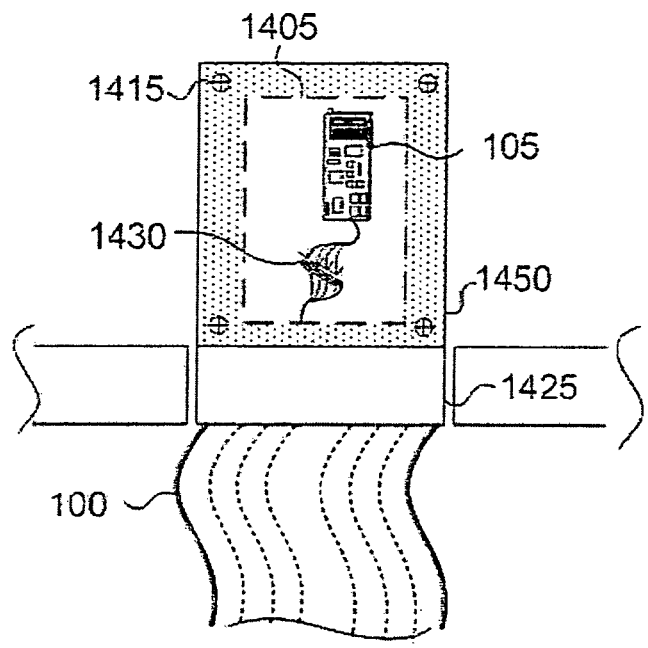
Figure 14C:
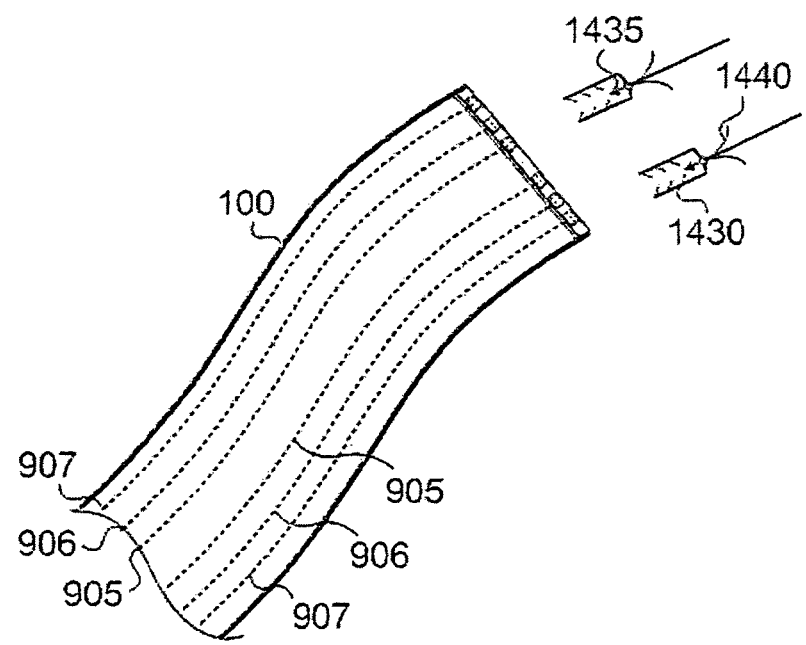

In this exemplary embodiment, the installer must cut a square hole in the drywall slightly larger than the outer dimensions of the enclosure box 1405 and then cut a second hole 1408 large enough to allow a flexible RFID floor covering product to pass inside the wall underneath the base molding 1425. FIG. 14A shows several clamp connectors 1430 hanging from the bottom of the enclosure box 1405. FIG. 14B presents a front view of the circuit board 105 and base molding 1425. If the RFID floor covering product is rigid (e.g. laminated wood), then the clamp connectors 1430 must be pulled thorough the hole 1408 and connected to the floor antenna 100 under the base molding 1425. FIG. 14C presents one of many possible connector designs. Each clamp connector 1430 is shown with a tapered needle 1435 that can be inserted into the edge of the RFID floor covering product to make electrical contact with one of the open ends of conductive leads 905, 906, and 907. Squeezing the clamp holder 1440 opens the end of the connector, and releasing the clamp holder 1440 allows the metal barbs inside the mouth of the connector to penetrate into the top and bottom surfaces of the RFID floor covering, making it difficult for the clamp connector to be pulled away from the floor covering. Each clamp connector 1430 has an electrical wire that connects to a connector block 1445 at the bottom surface of the enclosure box 1405. Inside the enclosure box 1405, circuit board 105 also connects to the connector block 1445, thereby connecting the circuit board 105 to each of the open ends of the U-shaped leads 905, 906, and 907. One of ordinary skill will appreciate that there are many means, ways and devices that may be used to connect the open ends of leads 905, 906, and 907 to the circuit board 105. As discussed above, the interconnections 925 can be provided by the circuit board 105 to create a spiral antenna. An installer may finish the installation by attaching screws 1415 through the cover plate 1450 to each clamp 1410. As exemplified in FIGS. 14A and 14B, the section of base molding 1425 may be attached to the cover plate 1450.

The circuit board 105 may have a switch 1455, for example a ten-position switch, used to adjust the impedance of the transceiver circuit and increase the power transfer between the floor antenna 100 and the transceiver circuit 105. The instructions for selecting the position of this switch 1455 can be printed on the back surface of the face plate 1450. The optimum position of this switch 1455 will depend where the floor covering is cut, i.e. the location of cut 915 in FIG. 9. The back of the RFID floor covering product can be marked by dashed lines with printed instructions indicating the best switch setting for the cut length of floor covering.

Throughout the description and claims of this specification, the words "comprise," "contain," and "include," (and variations of the words, for example "comprising" and "comprises,") mean "including but not limited to," and are not intended to (and do not) exclude other components, integers, moieties, additives or steps. Throughout the description and claims of this specification, the word "a" means "one or more" and is not intended to mean "only one." Although various embodiments have been described and illustrated, it is to be understood that a variety of changes and modifications may be made by one of ordinary skill in the related art without departing from the scope or spirit of the invention. All such changes and modifications are intended to be included within the scope of the invention as defined by the claims. The described embodiments are to be considered in all respects only as illustrative, and not restrictive, and all changes within the meaning and range of equivalency of the claims are to be embraced within that scope.

The invention claimed is:

1. A system for monitoring and responding to predefined movements of a monitored person within premises occupied by the person, comprising:
    an upper-body RFID tag and a lower-body RFID tag, wherein the upper-body RFID tag is distinguishable from the lower-body RFID tag as a fall tag;
    a plurality of RFID antennas located in the premises comprising at least one RFID floor antenna associated with flooring in the premise, at least one RFID bed antenna associated with a bed assigned to the person, and at least one RFID door antenna associated with a doorknob or doorway providing egress from the premises;
        one or more controllers electrically connected to the plurality of RFID antennas and configured to receive signals received from the upper-body RFID tag and the lower-body RFID tag, the one or more controllers further configured to
        determine a fall has occurred when the upper-body RFID tag remains close to the RFID floor antenna, and
        determine unauthorized movement of the monitored person has occurred according to detection of the lower-body RFID tag in proximity to one or more of the plurality of RFID antennas; and
    a response system configured to implement one or more response actions in response to detecting the fall or unauthorized movement.

2. The system of claim 1, wherein the response actions comprise transmitting an attendant call message associated with an alert activated in response to the detected fall or unauthorized movement, and recording attendant response times based in the detection of the arrival of an RFID tag worn by an attendant at the premises in response to the call message.

3. The system of claim 1, wherein:
    the controller is configured to detect a fall from which the person has not recovered by detecting that the upper-body RFID tag worn by the monitored person has entered into close proximity to the RFID floor antenna for a predetermined period of time that may be customized according to the monitored person.

4. The system of claim 1, wherein:
    the RFID bed antenna comprises an RFID antenna located in or attached to a bed frame or mattress associated with the bed assigned to the person for sleeping within the premises;
    the controller is configured to detect bed egress by detecting when the lower-body RFID tag worn by the person has moved past a read range of the RFID bed antenna; and
    the response actions comprise transmission of a bed egress message to a patient monitoring system.

5. The system of claim 1, wherein:
    the upper-body RFID tag is configured as a wrist tag worn on a wrist of the monitored person;
    the controller is configured to detect attempted room egress by detecting that the wrist tag worn by the monitored person has moved into close proximity to the door antenna associated with the doorknob of a door providing egress to the premises; and
    the response actions comprise activation of a pre-recorded or voice synthesized voice message that warns the monitored person with respect to unauthorized egress, the pre-recorded or voice synthesized voice message being in a preferred language associated with the monitored person and at a volume level adjusted by the controller for any hearing impairments associated with the monitored person.

6. The system of claim 1, wherein:
    the plurality of RFID antennas further comprises an RFID antenna associated with medication;
    the controller is further configured to detect an authorized medication access by detecting that the upper-body RFID tag worn by the person has moved into close proximity to the RFID antenna associated with the medication that the person is authorized to access; and
    the response actions comprise transmitting an authorized medication access message to the patient monitoring system.

7. The system of claim 1, further comprising:
    an RFID tag or barcode label associated with medication within the premises associated with the monitored person;
    wherein the controller is further configured to detect each medication delivery to the monitored person by detecting that the RFID tag or barcode label associated with the medication has moved into close proximity with the RFID bed antenna or barcode reader in order to determine whether the medication has been delivered within a predetermined dosage time associated with the medication; and
    the response actions comprise recording or transmitting a late medication delivery indication in response to a determination that the medication has not been delivered until after the predetermined dosage time.

8. The system of claim 1, wherein the RFID bed antenna comprises an RFID antenna printed on or affixed to a mattress cover or mattress pad.

9. The system of claim 1, wherein the RFID bed antenna comprises an RFID bed frame antenna located with or attached to a bed frame supporting a mattress, further comprising a conductive shield located under or within the mattress, a mattress cover or mattress pad, wherein the conductive shield is configured to prevent the RFID bed frame antenna from detecting the presence of a body-worn RFID tag located above the conductive shield until the body-worn RFID tag moves away from the conductive shield and into close proximity to the RFID bed frame antenna.

10. The system of claim 1, wherein the RFID floor antenna comprises conductive leads affixed to flooring sections, floor tiles, carpet backing, underlayment pad or a polymer fabric associated with flooring within the premises.

11. The system of claim 1, wherein the RFID floor antenna comprises concentric U-shaped conductive leads located under or within a flooring component such that each concentric U-shaped conductive lead comprises two open ends that each abut an edge of the flooring component, and an edge connector configured for connection to the edge of the flooring component that electrically connects the U-shaped conductive leads into a continuous spiral antenna.

12. The system of claim 1, further comprising an RFID antenna located in a portable bathroom mat configured for detecting a fall within a bathroom in which the bathroom mat is located.

13. The system of claim 1, further comprising an RFID antenna located within or under a shower stall or tub configured for detecting a fall within the shower stall or tub.

14. The system of claim 1, wherein the response action comprises transmission of a fall alert message which is repeated at periodic intervals until an RFID tag worn by an attendant is detected in close proximity to the monitored person.

15. The system of claim 1, wherein:
the RFID bed antenna comprises an RFID antenna located in or attached to a bed frame or mattress associated with the bed assigned to the person for sleeping within the premises;
when "electronic bed restraint" has been ordered, the one or more response actions comprise a pre-recorded or synthesized voice message in a preferred language of the monitored person and at a volume level appropriate for any hearing impairments identified for the monitored person, wherein the voice message requests the monitored person to remain in the bed.

16. The system of claim 1, wherein:
the at least one RFID floor antenna comprises two RFID floor antennas positioned proximate to the doorway providing egress from the premises, and
the controller is configured to detect attempted room egress by detecting that the lower-body RFID tag worn by the monitored person has moved through close proximity with the two RFID floor antennas in a direction toward room egress;
the response actions comprise activation of a pre-recorded or voice synthesized voice message that warns the monitored person with respect to unauthorized egress, the pre-recorded or voice synthesized voice message being in a preferred language associated with the monitored person and at a volume level adjusted by the controller for any hearing impairments associated with the monitored person.

17. A system for monitoring and responding to a fall from which a monitored person has not recovered within premises occupied by the person, comprising:
a body-worn RFID fall tag;
one or more RFID floor antennas associated with flooring in the premise;
one or more controllers electrically connected to the one or more RFID floor antennas and configured to receive signals received from the body-worn RFID fall tag and to determine a fall has occurred when the body-worn RFID fall tag remains close to the one or more RFID floor antennas for a predetermined period of time according to a health condition of the monitored person; and
one or more response systems configured to activate one or more response actions in response to the determination that the monitored person has engaged in the fall from which the monitored person has not recovered.

18. The system of claim 17, wherein the response actions comprise transmitting a fall alert message to a patient monitoring system and detecting an RFID tag worn by an attending party entering into close proximity to the monitored person subsequent to the detected fall indicating that the attending party has responded to the fall alert message.

19. The system of claim 17, wherein the floor RFID antennas comprise a first floor antenna located in a bathroom mat located in a bathroom within the premises configured to detect a fall in the bathroom, and a second floor antenna comprising antenna leads located under or within a shower or bathtub to detect falls while bathing.

20. An RFID floor antenna system configured for communication with a body-worn RFID tag for detecting a fall of a monitored person within premises occupied by the person, comprising:
a floor covering; a plurality of concentric U-shaped conductive leads located within the floor covering, wherein each of the concentric U-shaped conductive leads comprises two open ends that abut an edge of the floor covering, and wherein cutting off a side of the floor covering parallel to the edge shortens a length of each of the plurality of concentric U-shaped conductive leads while maintaining a quantity of the concentric U-shaped conductive leads and allowing the open ends of the concentric U-shaped conductive leads to be electrically interconnected to create a multi-loop spiral antenna communicating with said body-worn RFID tag in detecting said fall of said monitored person.

21. The system of claim 20, further comprising:
a circuit board configured for connection to an edge connector and comprising circuitry configured to electrically interconnect the plurality of concentric U-shaped conductive leads into the multi-loop spiral antenna,
wherein the edge connector comprises a plurality of needle contacts configured to penetrate the floor covering to make electrical contact with the open ends of the concentric U-shaped conductive leads.

* * * * *